United States Patent
Burbidge et al.

(10) Patent No.: US 8,227,576 B2
(45) Date of Patent: Jul. 24, 2012

(54) ANTIBODIES AGAINST AMYLOID-β PEPTIDE

(75) Inventors: Stephen Anthony Burbidge, Harlow (GB); Jonathan Henry Ellis, Stevenage (GB); Susannah K Ford, Stevenage (GB); Volker Germaschewski, Stevenage (GB); Umesh Kumar, Harlow (GB); Karen Louise Philpott, Harlow (GB); Peter Ernest Soden, Harlow (GB)

(73) Assignee: Glaxo Group Limited (GB)

( * ) Notice: Subject to any disclaimer, the term of this patent is extended or adjusted under 35 U.S.C. 154(b) by 823 days.

(21) Appl. No.: 12/294,438

(22) PCT Filed: Mar. 27, 2007

(86) PCT No.: PCT/EP2007/052928
§ 371 (c)(1), (2), (4) Date: Sep. 25, 2008

(87) PCT Pub. No.: WO2007/113172
PCT Pub. Date: Oct. 11, 2007

(65) Prior Publication Data
US 2011/0142824 A1 Jun. 16, 2011

Related U.S. Application Data

(60) Provisional application No. 60/787,588, filed on Mar. 30, 2006.

(51) Int. Cl.
C12P 21/08 (2006.01)
C07K 16/00 (2006.01)
A61K 39/395 (2006.01)
A61K 39/00 (2006.01)

(52) U.S. Cl. ............... 530/387.3; 530/387.1; 530/388.1; 424/130.1; 424/133.1; 424/141.1

(58) Field of Classification Search .................. None
See application file for complete search history.

(56) References Cited

U.S. PATENT DOCUMENTS 5,773,218 A * 6/1998 Gallatin et al. ............... 435/6.11
6,787,519 B2 * 9/2004 Huang et al. ................. 514/17.8
2002/0155426 A1 * 10/2002 Cordell et al. .................... 435/4

FOREIGN PATENT DOCUMENTS

WO  WO2004/032868  4/2004
WO  WO2004/080419  9/2004

OTHER PUBLICATIONS

Rudikoff, Giusti, Cook, and Scharff. Single amino acid substitution altering antigen-binding specificity. Proceedings of the National Academy of Science, 1982. vol. 79, pp. 1979-1983.*
Mac Callum, Martin, and Thornton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*
Wu, Nie, Huse, and Watkins. Humanization of a murine monoclonal antibody by simultaneous optimization of framework and CDR residues. Journal of Molecular Biology, 1999. vol. 294, pp. 151-162.*
Reiger, Michaelis, and Green. Glossary of Genetics and Cytogenetics, 4th Ed., Springer-Verlay, Berlin, 1976. pp. 17-18.*
Morgan, et al., "The N-terminal end of the $C_H2$ domain of chimeric human IgGI anti-HLA-DR is necessary for C1q, FcγRI and FcγRIII binding." *Immunology* (1995) 86:319-324.

* cited by examiner

*Primary Examiner* — Anne M. Gussow
(74) *Attorney, Agent, or Firm* — Johnathan M. Dermott; William T. Han

(57) ABSTRACT

Antibodies that bind human β-amyloid peptide, methods of treating diseases or disorders characterised by elevated β-amyloid levels or β-amyloid deposits with said antibodies, pharmaceutical compositions comprising said antibodies and methods of manufacture.

18 Claims, No Drawings

SEQUENCE LISTING

<160> NUMBER OF SEQ ID NOS: 44

<210> SEQ ID NO 1
<211> LENGTH: 5
<212> TYPE: PRT
<213> ORGANISM: Mouse

<400> SEQUENCE: 1

Asp Asn Gly Met Ala
 1               5

<210> SEQ ID NO 2
<211> LENGTH: 17
<212> TYPE: PRT
<213> ORGANISM: Mouse

<400> SEQUENCE: 2

Phe Ile Ser Asn Leu Ala Tyr Ser Ile Asp Tyr Ala Asp Thr Val Thr
 1               5                  10                  15

Gly

<210> SEQ ID NO 3
<211> LENGTH: 6
<212> TYPE: PRT
<213> ORGANISM: Mouse

<400> SEQUENCE: 3

Gly Thr Trp Phe Ala Tyr
 1               5

<210> SEQ ID NO 4
<211> LENGTH: 16
<212> TYPE: PRT
<213> ORGANISM: Mouse

<400> SEQUENCE: 4

Arg Val Ser Gln Ser Leu Leu His Ser Asn Gly Tyr Thr Tyr Leu His
 1               5                  10                  15

<210> SEQ ID NO 5
<211> LENGTH: 7
<212> TYPE: PRT
<213> ORGANISM: Mouse

<400> SEQUENCE: 5

Lys Val Ser Asn Arg Phe Ser
 1               5

<210> SEQ ID NO 6
<211> LENGTH: 9
<212> TYPE: PRT
<213> ORGANISM: Mouse

<400> SEQUENCE: 6

Ser Gln Thr Arg His Val Pro Tyr Thr
 1               5

<210> SEQ ID NO 7
<211> LENGTH: 16
<212> TYPE: PRT
<213> ORGANISM: Artificial Sequence
<220> FEATURE:
<223> OTHER INFORMATION: 16mer peptide containing residues 1-10 of beta
      amyloid peptide

```
<220> FEATURE:
<221> NAME/KEY: MOD_RES
<222> LOCATION: (16)...(16)
<223> OTHER INFORMATION: Biotinylated

<400> SEQUENCE: 7

Asp Ala Glu Phe Arg His Asp Ser Gly Tyr Gly Ser Gly Gly Ser Lys
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: 16mer peptide containing residues 1-9 of beta
      amyloid peptide
<220> FEATURE:
<221> NAME/KEY: MOD_RES
<222> LOCATION: (16)...(16)
<223> OTHER INFORMATION: Biotinylated

<400> SEQUENCE: 8

Asp Ala Glu Phe Arg His Asp Ser Gly Gly Ser Gly Ser Gly Ser Lys
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: 16mer peptide containing residues 1-8 of beta
      amyloid peptide
<220> FEATURE:
<221> NAME/KEY: MOD_RES
<222> LOCATION: (16)...(16)
<223> OTHER INFORMATION: Biotinylated

<400> SEQUENCE: 9

Asp Ala Glu Phe Arg His Asp Ser Gly Ser Gly Gly Ser Gly Gly Lys
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: 16mer peptide containing residues 1-7 of beta
      amyloid peptide
<220> FEATURE:
<221> NAME/KEY: MOD_RES
<222> LOCATION: (16)...(16)
<223> OTHER INFORMATION: Biotinylated

<400> SEQUENCE: 10

Asp Ala Glu Phe Arg His Asp Gly Ser Gly Gly Ser Gly Gly Ser Lys
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: 16mer peptide containing residues 1-6 of beta
      amyloid peptide
<220> FEATURE:
<221> NAME/KEY: MOD_RES
<222> LOCATION: (16)...(16)
<223> OTHER INFORMATION: Biotinylated

<400> SEQUENCE: 11

Asp Ala Glu Phe Arg His Gly Ser Gly Gly Ser Gly Gly Ser Gly Lys
```

<210> SEQ ID NO 12
<211> LENGTH: 16
<212> TYPE: PRT
<213> ORGANISM: Artificial Sequence
<220> FEATURE:
<223> OTHER INFORMATION: 16mer peptide containing residues 1-5 of beta amyloid peptide
<220> FEATURE:
<221> NAME/KEY: MOD_RES
<222> LOCATION: (16)...(16)
<223> OTHER INFORMATION: Biotinylated

<400> SEQUENCE: 12

Asp Ala Glu Phe Arg Gly Ser Gly Gly Ser Gly Gly Ser Gly Ser Lys
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: 16mer peptide containing residues 1-4 of beta amyloid peptide
<220> FEATURE:
<221> NAME/KEY: MOD_RES
<222> LOCATION: (16)...(16)
<223> OTHER INFORMATION: Biotinylated

<400> SEQUENCE: 13

Asp Ala Glu Phe Gly Ser Gly Gly Ser Gly Gly Ser Gly Gly Ser Lys
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: 16mer peptide containing residues 1-3 of beta amyloid peptide
<220> FEATURE:
<221> NAME/KEY: MOD_RES
<222> LOCATION: (16)...(16)
<223> OTHER INFORMATION: Biotinylated

<400> SEQUENCE: 14

Asp Ala Glu Gly Ser Gly Gly Ser Gly Gly Ser Gly Gly Ser Gly Lys
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: 16mer peptide containing residues 1-12 of beta amyloid peptide
<220> FEATURE:
<221> NAME/KEY: MOD_RES
<222> LOCATION: (16)...(16)
<223> OTHER INFORMATION: Biotinylated

<400> SEQUENCE: 15

Asp Ala Glu Phe Arg His Asp Ser Gly Tyr Glu Val Gly Ser Gly Lys
1               5                   10                  15

<210> SEQ ID NO 16
<211> LENGTH: 16
<212> TYPE: PRT
<213> ORGANISM: Artificial Sequence
<220> FEATURE:

```
<223> OTHER INFORMATION: Peptide APP1
<220> FEATURE:
<221> NAME/KEY: MOD_RES
<222> LOCATION: (16)...(16)
<223> OTHER INFORMATION: Biotinylated

<400> SEQUENCE: 16

Ser Glu Val Lys Met Asp Ala Glu Phe Arg His Asp Gly Ser Gly Lys
1               5                   10                  15

<210> SEQ ID NO 17
<211> LENGTH: 115
<212> TYPE: PRT
<213> ORGANISM: Mouse

<400> SEQUENCE: 17

Glu Val Lys Leu Val Glu Ser Gly Gly Gly Leu Val Gln Pro Gly Gly
1               5                   10                  15

Ser Leu Lys Leu Ser Cys Ala Val Ser Gly Phe Thr Phe Ser Asp Asn
            20                  25                  30

Gly Met Ala Trp Val Arg Gln Ala Pro Arg Lys Gly Pro Glu Trp Ile
        35                  40                  45

Ala Phe Ile Ser Asn Leu Ala Tyr Ser Ile Asp Tyr Ala Asp Thr Val
    50                  55                  60

Thr Gly Arg Phe Thr Ile Ser Arg Asp Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Val Ser Gly Thr Trp Phe Ala Tyr Trp Gly Gln Gly Thr Leu Val Thr
            100                 105                 110

Val Ser Ala
        115

<210> SEQ ID NO 18
<211> LENGTH: 345
<212> TYPE: DNA
<213> ORGANISM: Mouse

<400> SEQUENCE: 18
gaggtgaagc tggtggagtc tgggggaggc ttagtgcagc ctggagggtc cctgaaactc      60
tcctgtgcag tctctggatt cactttcagt gacaacggaa tggcgtgggt tcgacaggct     120
ccaaggaagg ggcctgagtg gatagcgttc attagtaatt tggcatatag tatcgactac     180
gcagacactg tgacgggccg attcaccatc tctagagata atgccaagaa taccctgtac     240
ctggaaatga gcagtctgag gtctgaggac acggccatgt actattgtgt aagcgggacc     300
tggtttgctt actggggcca aggactctg gtcactgtct ctgca                      345

<210> SEQ ID NO 19
<211> LENGTH: 112
<212> TYPE: PRT
<213> ORGANISM: Mouse

<400> SEQUENCE: 19

Asp Val Val Leu Thr Gln Thr Pro Leu Ser Leu Pro Val Ser Leu Gly
1               5                   10                  15

Asp Gln Ala Ser Ile Ser Cys Arg Val Ser Gln Ser Leu Leu His Ser
            20                  25                  30

Asn Gly Tyr Thr Tyr Leu His Trp Tyr Leu Gln Lys Pro Gly Gln Ser
        35                  40                  45
```

-continued

```
Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Arg His Val Pro Tyr Thr Phe Gly Gly Gly Thr Lys Leu Glu Ile Lys
                100                 105                 110

<210> SEQ ID NO 20
<211> LENGTH: 336
<212> TYPE: DNA
<213> ORGANISM: Mouse

<400> SEQUENCE: 20
gatgttgtgc tgacccaaac tccactctcc ctgcctgtca gtcttggaga tcaagcctcc      60
atctcttgca gagttagtca gagcctttta cacagtaatg atacaccta tttacattgg     120 tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaactag acatgttccg     300
tacacgttcg gaggggggac caagctggaa ataaaa                               336

<210> SEQ ID NO 21
<211> LENGTH: 98
<212> TYPE: PRT
<213> ORGANISM: Human

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Tyr Ile Ser Ser Ser Ser Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 22
<211> LENGTH: 296
<212> TYPE: DNA
<213> ORGANISM: Human

<400> SEQUENCE: 22
gaggtgcagc tggtggagtc tgggggaggc ttggtacagc ctggggggtc cctgagactc      60
tcctgtgcag cctctggatt caccttcagt agctatagca tgaactgggt ccgccaggct     120
ccagggaagg ggctggagtg ggtttcatac attagtagta gtagtagtac catatactac     180
gcagactctg tgaagggccg attcaccatc tccagagaca atgccaagaa ctcactgtat     240
ctgcaaatga acagcctgag agccgaggac acggctgtgt attactgtgc gagaga         296

<210> SEQ ID NO 23
```

```
<211> LENGTH: 15
<212> TYPE: PRT
<213> ORGANISM: Human

<400> SEQUENCE: 23

Tyr Phe Asp Tyr Trp Gly Gln Gly Thr Leu Val Thr Val Ser Ser
1               5                   10                  15

<210> SEQ ID NO 24
<211> LENGTH: 112
<212> TYPE: PRT
<213> ORGANISM: Human

<400> SEQUENCE: 24

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 25
<211> LENGTH: 336
<212> TYPE: DNA
<213> ORGANISM: Human

<400> SEQUENCE: 25
gatattgtga tgactcagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgatct atttgggttc taatcgggcc     180 tccgggtcc ctgacaggtt cagtggcagt ggatcaggca cagattttac actgaaaatc      240
agcagagtgg aggctgagga tgttggggtt tattactgca tgcaagctct acaaactccg     300
tggacgttcg gccaagggac caaggtggaa atcaaa                                336

<210> SEQ ID NO 26
<211> LENGTH: 115
<212> TYPE: PRT
<213> ORGANISM: Artificial Sequence
<220> FEATURE:
<223> OTHER INFORMATION: Humanised

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Gly Met Ala Trp Val Arg Gln Ala Pro Gly Lys Gly Leu Glu Trp Val
        35                  40                  45

Ser Phe Ile Ser Asn Leu Ala Tyr Ser Ile Asp Tyr Ala Asp Thr Val
    50                  55                  60
```

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Ser Gly Thr Trp Phe Ala Tyr Trp Gly Gln Gly Thr Leu Val Thr
            100                 105                 110

Val Ser Ser
        115

<210> SEQ ID NO 27
<211> LENGTH: 345
<212> TYPE: DNA
<213> ORGANISM: Human

<400> SEQUENCE: 27
gaggtgcagc tggtggagtc tggggggaggc ttggtacagc ctggggggtc cctgagactc     60
tcctgtgcag cctctggatt caccttcagt gacaacggaa tggcgtgggt ccgccaggct    120
ccagggaagg ggctggagtg ggtttcattc attagtaatt ggcatatag tatcgactac    180
gcagacactg tgacgggccg attcaccatc tccagagaca tgccaagaa ctcactgtat    240
ctgcaaatga acagcctgag agccgaggac acggctgtgt attactgtgt cagcgggacc    300
tggtttgctt actggggcca gggcacacta gtcacagtct cctca                    345

<210> SEQ ID NO 28
<211> LENGTH: 115
<212> TYPE: PRT
<213> ORGANISM: Human

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asp Asn
            20                  25                  30

Gly Met Ala Trp Val Arg Gln Ala Pro Gly Lys Gly Leu Glu Trp Val
        35                  40                  45

Ser Phe Ile Ser Asn Leu Ala Tyr Ser Ile Asp Tyr Ala Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Ser Gly Thr Trp Phe Ala Tyr Trp Gly Gln Gly Thr Leu Val Thr
            100                 105                 110

Val Ser Ser
        115

<210> SEQ ID NO 29
<211> LENGTH: 345
<212> TYPE: DNA
<213> ORGANISM: Human

<400> SEQUENCE: 29
gaggtgcagc tggtggagtc tggggggaggc ttggtacagc ctggggggtc cctgagactc     60
tcctgtgcag tctctggatt caccttcagt gacaacggaa tggcgtgggt ccgccaggct    120
ccagggaagg ggctggagtg ggtttcattc attagtaatt ggcatatag tatcgactac    180
gcagacactg tgacgggccg attcaccatc tccagagaca tgccaagaa ctcactgtat    240

```
ctgcaaatga acagcctgag agccgaggac acggctgtgt attactgtgt cagcgggacc    300
tggtttgctt actggggcca gggcacacta gtcacagtct cctca                    345
```

<210> SEQ ID NO 30
<211> LENGTH: 115
<212> TYPE: PRT
<213> ORGANISM: Human

<400> SEQUENCE: 30

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Asn
            20                  25                  30

Gly Met Ala Trp Val Arg Gln Ala Pro Gly Lys Gly Leu Glu Trp Ile
        35                  40                  45

Ser Phe Ile Ser Asn Leu Ala Tyr Ser Ile Asp Tyr Ala Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Ser Gly Thr Trp Phe Ala Tyr Trp Gly Gln Gly Thr Leu Val Thr
            100                 105                 110

Val Ser Ser
        115
```

<210> SEQ ID NO 31
<211> LENGTH: 345
<212> TYPE: DNA
<213> ORGANISM: Human

<400> SEQUENCE: 31

```
gaggtgcagc tggtggagtc tgggggaggc ttggtacagc ctggggggtc cctgagactc     60
tcctgtgcag cctctggatt caccttcagt gacaacggaa tggcgtgggt ccgccaggct    120
ccagggaagg ggctggagtg gatctcattc attagtaatt tggcatatag tatcgactac    180
gcagacactg tgacgggccg attcaccatc tccagagaca atgccaagaa ctcactgtat    240
ctgcaaatga acagcctgag agccgaggac acggctgtgt attactgtgt cagcgggacc    300
tggtttgctt actggggcca gggcacacta gtcacagtct cctca                    345
```

<210> SEQ ID NO 32
<211> LENGTH: 112
<212> TYPE: PRT
<213> ORGANISM: Human

<400> SEQUENCE: 32

```
Asp Ile Val Met Thr Gln Ser Pro Leu Ser Leu Pro Val Thr Pro Gly
 1               5                  10                  15

Glu Pro Ala Ser Ile Ser Cys Arg Val Ser Gln Ser Leu Leu His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
```

```
                    85                  90                  95
Arg His Val Pro Tyr Thr Phe Gly Gly Gly Thr Lys Val Glu Ile Lys
            100                 105                 110

<210> SEQ ID NO 33
<211> LENGTH: 336
<212> TYPE: DNA
<213> ORGANISM: Human

<400> SEQUENCE: 33
gatattgtga tgactcagtc tccactctcc ctgcccgtca cccctggaga gccggcctcc      60
atctcctgca gagttagtca gagccttttta cacagtaatg gatacaccta tttacattgg    120
tacctgcaga agccagggca gtctccacag ctcctgatct ataaagtttc caaccgattt     180 tctgggtcc  ctgacaggtt cagtggcagt ggatcaggca cagattttac actgaaaatc     240
agcagagtgg aggctgagga tgttggggtt tattactgct ctcaaactag acatgttccg     300
tacacgttcg gcggagggac caaggtggaa atcaaa                               336

<210> SEQ ID NO 34
<211> LENGTH: 445
<212> TYPE: PRT
<213> ORGANISM: Human

<400> SEQUENCE: 34

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Asn
            20                  25                  30

Gly Met Ala Trp Val Arg Gln Ala Pro Gly Lys Gly Leu Glu Trp Val
        35                  40                  45

Ser Phe Ile Ser Asn Leu Ala Tyr Ser Ile Asp Tyr Ala Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Ser Gly Thr Trp Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255
```

Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Asp Glu Leu Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
    435                 440                 445

<210> SEQ ID NO 35
<211> LENGTH: 1335
<212> TYPE: DNA
<213> ORGANISM: Human

<400> SEQUENCE: 35
gaggtgcagc tggtggagtc tgggggaggc ttggtacagc ctggggggtc cctgagactc      60
tcctgtgcag cctctggatt caccttcagt gacaacggaa tggcgtgggt ccgccaggct     120
ccagggaagg ggctggagtg ggtttcattc attagtaatt ggcatatag tatcgactac      180
gcagacactg tgacgggccg attcaccatc tccagagaca atgccaagaa ctcactgtat     240
ctgcaaatga acagcctgag agccgaggac acggctgtgt attactgtgt cagcgggacc     300
tggtttgctt actggggcca gggcacacta gtcacagtct cctcagcctc caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaactcgcgg ggcaccgtc agtcttcctc      720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca aagccctccc agcccccatc gagaaaacca tctccaaagc caaagggcag    1020
ccccgagaac cacaggtgta caccctgccc ccatcccggg atgagctgac caagaaccag    1080

```
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaa                                                     1335

<210> SEQ ID NO 36
<211> LENGTH: 445
<212> TYPE: PRT
<213> ORGANISM: Human

<400> SEQUENCE: 36
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Val | Ser | Gly | Phe | Thr | Phe | Ser | Asp | Asn |
| | | | 20 | | | | | 25 | | | | | 30 | | |
| Gly | Met | Ala | Trp | Val | Arg | Gln | Ala | Pro | Gly | Lys | Gly | Leu | Glu | Trp | Val |
| | | 35 | | | | | 40 | | | | | 45 | | | |
| Ser | Phe | Ile | Ser | Asn | Leu | Ala | Tyr | Ser | Ile | Asp | Tyr | Ala | Asp | Thr | Val |
| | 50 | | | | | 55 | | | | | 60 | | | | |
| Thr | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Val | Ser | Gly | Thr | Trp | Phe | Ala | Tyr | Trp | Gly | Gln | Gly | Thr | Leu | Val | Thr |
| | | | 100 | | | | | 105 | | | | | 110 | | |
| Val | Ser | Ser | Ala | Ser | Thr | Lys | Gly | Pro | Ser | Val | Phe | Pro | Leu | Ala | Pro |
| | | 115 | | | | | 120 | | | | | 125 | | | |
| Ser | Ser | Lys | Ser | Thr | Ser | Gly | Gly | Thr | Ala | Ala | Leu | Gly | Cys | Leu | Val |
| | 130 | | | | | 135 | | | | | 140 | | | | |
| Lys | Asp | Tyr | Phe | Pro | Glu | Pro | Val | Thr | Val | Ser | Trp | Asn | Ser | Gly | Ala |
| 145 | | | | | 150 | | | | | 155 | | | | | 160 |
| Leu | Thr | Ser | Gly | Val | His | Thr | Phe | Pro | Ala | Val | Leu | Gln | Ser | Ser | Gly |
| | | | | 165 | | | | | 170 | | | | | 175 | |
| Leu | Tyr | Ser | Leu | Ser | Ser | Val | Val | Thr | Val | Pro | Ser | Ser | Ser | Leu | Gly |
| | | | 180 | | | | | 185 | | | | | 190 | | |
| Thr | Gln | Thr | Tyr | Ile | Cys | Asn | Val | Asn | His | Lys | Pro | Ser | Asn | Thr | Lys |
| | | 195 | | | | | 200 | | | | | 205 | | | |
| Val | Asp | Lys | Lys | Val | Glu | Pro | Lys | Ser | Cys | Asp | Lys | Thr | His | Thr | Cys |
| | 210 | | | | | 215 | | | | | 220 | | | | |
| Pro | Pro | Cys | Pro | Ala | Pro | Glu | Leu | Ala | Gly | Ala | Pro | Ser | Val | Phe | Leu |
| 225 | | | | | 230 | | | | | 235 | | | | | 240 |
| Phe | Pro | Pro | Lys | Pro | Lys | Asp | Thr | Leu | Met | Ile | Ser | Arg | Thr | Pro | Glu |
| | | | | 245 | | | | | 250 | | | | | 255 | |
| Val | Thr | Cys | Val | Val | Val | Asp | Val | Ser | His | Glu | Asp | Pro | Glu | Val | Lys |
| | | | 260 | | | | | 265 | | | | | 270 | | |
| Phe | Asn | Trp | Tyr | Val | Asp | Gly | Val | Glu | Val | His | Asn | Ala | Lys | Thr | Lys |
| | | 275 | | | | | 280 | | | | | 285 | | | |
| Pro | Arg | Glu | Glu | Gln | Tyr | Asn | Ser | Thr | Tyr | Arg | Val | Val | Ser | Val | Leu |
| | 290 | | | | | 295 | | | | | 300 | | | | |
| Thr | Val | Leu | His | Gln | Asp | Trp | Leu | Asn | Gly | Lys | Glu | Tyr | Lys | Cys | Lys |
| 305 | | | | | 310 | | | | | 315 | | | | | 320 |
| Val | Ser | Asn | Lys | Ala | Leu | Pro | Ala | Pro | Ile | Glu | Lys | Thr | Ile | Ser | Lys |

```
                325             330             335
Ala Lys Gly Gln Pro Arg Glu Pro Gln Val Tyr Thr Leu Pro Pro Ser
            340             345             350
Arg Asp Glu Leu Thr Lys Asn Gln Val Ser Leu Thr Cys Leu Val Lys
            355             360             365
Gly Phe Tyr Pro Ser Asp Ile Ala Val Glu Trp Glu Ser Asn Gly Gln
        370             375             380
Pro Glu Asn Asn Tyr Lys Thr Thr Pro Pro Val Leu Asp Ser Asp Gly
385             390             395             400
Ser Phe Phe Leu Tyr Ser Lys Leu Thr Val Asp Lys Ser Arg Trp Gln
                405             410             415
Gln Gly Asn Val Phe Ser Cys Ser Val Met His Glu Ala Leu His Asn
            420             425             430
His Tyr Thr Gln Lys Ser Leu Ser Leu Ser Pro Gly Lys
        435             440             445

<210> SEQ ID NO 37
<211> LENGTH: 1335
<212> TYPE: DNA
<213> ORGANISM: Human

<400> SEQUENCE: 37
```

| | | |
|---|---|---|
| gaggtgcagc tggtggagtc tgggggaggc ttggtacagc ctggggggtc cctgagactc | 60 |
| tcctgtgcag tctctggatt caccttcagt gacaacggaa tggcgtgggt ccgccaggct | 120 |
| ccagggaagg gctggagtg gtttcattc attagtaatt ggcatatag tatcgactac | 180 |
| gcagacactg tgacgggccg attcaccatc tccagagaca atgccaagaa ctcactgtat | 240 |
| ctgcaaatga acagcctgag agccgaggac acggctgtgt attactgtgt cagcgggacc | 300 |
| tggtttgctt actggggcca gggcacacta gtcacagtct cctcagcctc caccaagggc | 360 |
| ccatcggtct tccccctggc accctcctcc aagagcacct ctgggggcac agcggccctg | 420 |
| ggctgcctgg tcaaggacta cttccccgaa ccggtgacgg tgtcgtggaa ctcaggcgcc | 480 |
| ctgaccagcg gcgtgcacac cttcccggct gtcctacagt cctcaggact ctactccctc | 540 |
| agcagcgtgg tgaccgtgcc ctccagcagc ttgggcaccc agacctacat ctgcaacgtg | 600 |
| aatcacaagc ccagcaacac caaggtggac aagaaagttg agcccaaatc ttgtgacaaa | 660 |
| actcacacat gcccaccgtg cccagcacct gaactcgcgg ggcaccgtc agtcttcctc | 720 |
| ttccccccaa aacccaagga caccctcatg atctcccgga cccctgaggt cacatgcgtg | 780 |
| gtggtggacg tgagccacga agaccctgag gtcaagttca actggtacgt ggacggcgtg | 840 |
| gaggtgcata atgccaagac aaagccgcgg gaggagcagt acaacagcac gtaccgtgtg | 900 |
| gtcagcgtcc tcaccgtcct gcaccaggac tggctgaatg gcaaggagta caagtgcaag | 960 |
| gtctccaaca aagccctccc agcccccatc gagaaaacca tctccaaagc caaagggcag | 1020 |
| ccccgagaac acaggtgta caccctgccc ccatcccggg atgagctgac caagaaccag | 1080 |
| gtcagcctga cctgcctggt caaaggcttc tatcccagcg acatcgccgt ggagtgggag | 1140 |
| agcaatgggc agccggagaa caactacaag accacgcctc ccgtgctgga ctccgacggc | 1200 |
| tccttcttcc tctacagcaa gctcaccgtg gacaagagca ggtggcagca ggggaacgtc | 1260 |
| ttctcatgct ccgtgatgca tgaggctctg cacaaccact acacgcagaa gagcctctcc | 1320 |
| ctgtctccgg gtaaa | 1335 |

```
<210> SEQ ID NO 38
<211> LENGTH: 445
```

<212> TYPE: PRT
<213> ORGANISM: Human

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Gly Met Ala Trp Val Arg Gln Ala Pro Gly Lys Gly Leu Glu Trp Ile
        35                  40                  45

Ser Phe Ile Ser Asn Leu Ala Tyr Ser Ile Asp Tyr Ala Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Ser Gly Thr Trp Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 39
<211> LENGTH: 1335
<212> TYPE: DNA
<213> ORGANISM: Human

<400> SEQUENCE: 39
gaggtgcagc tggtggagtc tgggggaggc ttggtacagc ctggggggtc cctgagactc      60
tcctgtgcag cctctggatt caccttcagt gacaacggaa tggcgtgggt ccgccaggct     120
ccagggaagg gctgagtg gatctcattc attagtaatt tggcatatag tatcgactac      180
gcagacactg tgacgggccg attcaccatc tccagagaca atgccaagaa ctcactgtat     240
ctgcaaatga acagcctgag agccgaggac acggctgtgt attactgtgt cagcgggacc     300
tggtttgctt actggggcca gggcacacta gtcacagtct cctcagcctc caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgt gaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaactcgcgg gggcaccgtc agtcttcctc     720
ttccccccaa acccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca aagccctccc agccccatc gagaaaacca tctccaaagc caaagggcag    1020
ccccgagaac cacaggtgta caccctgccc ccatcccggg atgagctgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaa                                                    1335

<210> SEQ ID NO 40
<211> LENGTH: 219
<212> TYPE: PRT
<213> ORGANISM: Human

<400> SEQUENCE: 40

Asp Ile Val Met Thr Gln Ser Pro Leu Ser Leu Pro Val Thr Pro Gly
 1               5                  10                  15

Glu Pro Ala Ser Ile Ser Cys Arg Val Ser Gln Ser Leu Leu His Ser
            20                  25                  30

Asn Gly Tyr Thr Tyr Leu His Trp Tyr Leu Gln Lys Pro Gly Gln Ser
        35                  40                  45

```
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ser Gln Thr
                85                  90                  95
Arg His Val Pro Tyr Thr Phe Gly Gly Gly Thr Lys Val Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215

<210> SEQ ID NO 41
<211> LENGTH: 657
<212> TYPE: DNA
<213> ORGANISM: Human

<400> SEQUENCE: 41
gatattgtga tgactcagtc tccactctcc ctgcccgtca cccctggaga gccggcctcc      60
atctcctgca gagttagtca gagccttttta cacagtaatg gatacaccta tttacattgg    120
tacctgcaga agccagggca gtctccacag ctcctgatct ataaagtttc aaccgatttt    180
tctggggtcc ctgacaggtt cagtggcagt ggatcaggca cagattttac actgaaaatc    240
agcagagtgg aggctgagga tgttggggtt tattactgct ctcaaactag acatgttccg    300
tacacgttcg gcgagggac aaggtggaa atcaaacgta cggtggctgc accatctgtc      360
ttcatcttcc cgccatctga tgagcagttg aaatctggaa ctgcctctgt tgtgtgcctg    420
ctgaataact tctatcccag agaggccaaa gtacagtgga aggtggacaa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt       657

<210> SEQ ID NO 42
<211> LENGTH: 1335
<212> TYPE: DNA
<213> ORGANISM: Human

<400> SEQUENCE: 42
gaggtgcagc tggtggagtc tgcggcggga ctggtgcagc ctggcggcag cctgagactg      60
agctgtgccg tgtccggctt caccttcagc gacaacggca tggcctggt gaggcaggcc    120 cctggcaagg gcctggagtg ggtgtccttc atcagcaacc tggcctacag catcgactac    180
gccgacaccg tgaccggcag attcaccatc agccgggaca cgccaagaa cagcctgtac    240 ctgcagatga acagcctgag agccgaggac accgccgtgt actactgtgt gagcggcacc    300
```

```
tggttcgcct actggggcca gggcaccctg gtgaccgtgt ccagcgccag caccaagggc    360
cccagcgtgt tccccctggc ccccagcagc aagagcacca gcggcggcac agccgccctg    420
ggctgcctgg tgaaggacta cttccccgaa ccggtgaccg tgtcctggaa cagcggagcc    480
ctgaccagcg gcgtgcacac cttccccgcc gtgctgcaga gcagcggcct gtacagcctg    540
agcagcgtgg tgaccgtgcc cagcagcagc ctgggcaccc agacctacat ctgtaacgtg    600
aaccacaagc ccagcaacac caaggtggac aagaaggtgg agcccaagag ctgtgacaag    660
acccacacct gccccccctg ccctgccccc gagctggccg agcccccag cgtgttcctg     720 ttccccccca agcctaagga caccctgatg atcagcagaa ccccgaggt gacctgtgtg     780 gtggtggatg tgagccacga ggaccctgag gtgaagttca actggtacgt ggacggcgtg    840
gaggtgcaca atgccaagac caagcccagg gaggagcagt acaacagcac ctaccgggtg    900
gtgtccgtgc tgaccgtgct gcaccaggat tggctgaacg gcaaggagta caagtgtaag    960
gtgtccaaca aggccctgcc tgcccctatc gagaaaacca tcagcaaggc caagggccag   1020
cccagagagc cccaggtgta caccctgccc cctagcagag atgagctgac caagaaccag   1080
gtgtccctga cctgcctggt gaagggcttc taccccagcg acatcgccgt ggagtgggag   1140
agcaacggcc agcccgagaa caactacaag accaccccc ctgtgctgga cagcgatggc    1200
agcttcttcc tgtacagcaa gctgaccgtg gacaagagca gatggcagca gggcaacgtg   1260
ttcagctgct ccgtgatgca cgaggccctg cacaatcact acacccagaa gagcctgagc   1320
ctgtcccctg gcaag                                                    1335
```

<210> SEQ ID NO 43
<211> LENGTH: 657
<212> TYPE: DNA
<213> ORGANISM: Human

<400> SEQUENCE: 43

```
gacatcgtga tgacccagag ccccctgagc ctgcccgtga cccctggcga gcccgccagc     60
atcagctgta gagtgagcca gagcctgctg cacagcaacg gctacaccta cctgcactgg    120
tatctgcaga agcctggcca gagccctcag ctgctgatct acaaggtgtc caaccggttc    180
agcggcgtgc ctgatagatt cagcggcagc ggctccggca ccgacttcac cctgaagatc    240
agcagagtgg aggccgagga tgtgggcgtg tactactgct cccagaccag acacgtgcct    300
tacacctttg gcggcggaac aaaggtggag atcaagcgta cggtggccgc ccccagcgtg    360
ttcatcttcc cccccagcga tgagcagctg aagagcggca ccgccagcgt ggtgtgtctg    420
ctgaacaact tctaccccg ggaggccaag gtgcagtgga aggtggacaa tgccctgcag    480
agcggcaaca gccaggagag cgtgaccgag caggacagca aggactccac ctacagcctg    540
agcagcaccc tgaccctgag caaggccgac tacgagaagc acaaggtgta cgcctgtgag    600
gtgacccacc agggcctgtc cagccccgtg accaagagct tcaaccgggg cgagtgc       657
```

<210> SEQ ID NO 44
<211> LENGTH: 16
<212> TYPE: PRT
<213> ORGANISM: Artificial Sequence
<220> FEATURE:
<223> OTHER INFORMATION: 16mer peptide containing residues 2-13 of beta amyloid peptide
<220> FEATURE:
<221> NAME/KEY: MOD_RES
<222> LOCATION: (16)...(16)
<223> OTHER INFORMATION: Biotinylated

```
<400> SEQUENCE: 44

Ala Glu Phe Arg His Asp Ser Gly Tyr Glu Val His Gly Ser Gly Lys
1               5                   10                  15
```

ANTIBODIES AGAINST AMYLOID-β PEPTIDE

This application is a §371 national phase entry of International Application No. PCT/EP2007/052928, filed Mar. 27, 2007, which claims the benefit of US Provisional Application 60/787,588 filed Mar. 30, 2006.

FIELD OF THE INVENTION

The present invention relates to antibodies that bind β-amyloid peptide and in particular human β-amyloid peptide. The present invention also concerns methods of treating diseases or disorders characterised by elevated β-amyloid levels or β-amyloid deposits, particularly Alzheimer's disease, with said antibodies, pharmaceutical compositions comprising said antibodies and methods of manufacture. Other aspects of the present invention will be apparent from the description below.

BACKGROUND OF THE INVENTION

Alzheimer's disease (AD) is the most common cause of age-related cognitive decline, affecting greater than 12 million individuals worldwide (Citron M (2002) Nat. Neurosci 5, Suppl 1055-1057). The earliest stages of the disease are characterized by a progressive loss of memory with associated cognitive decline and language and behavioural deficits. In the later stages of the disease, patients develop global amnesia and have greatly reduced motor function. Death typically occurs 9 years following diagnosis and is often associated with other conditions, typically pneumonia (Davis K. L. and Samules S. C. (1998) in Pharmacological Management of Neurological and Psychiatric Disorders eds Enna S. J. and Coyle J. T. (McGraw-Hill, New York pp 267-316)). Current therapies represent symptomatic approaches, focussing on alleviating the cognitive impairment and ameliorating the behavioural symptoms associated with the progressing disease aetiology. In practice these treatments provide only a short lived cognitive benefit with the level of cognitive impairment reported only to last up to 2 years. The potential for a disease-modifying therapy that slows and possibly halts the progression of the disease is enormous. Such approaches would provide radical and sustained improvements to the quality of life of patients and importantly their careers as well as reducing the huge overall healthcare costs of this disease.

Clinical diagnosis of Alzheimer's disease is based upon a combination of physical and mental tests which lead to a diagnosis of possible or probable Alzheimer's disease. At post mortem the disease is confirmed by well characterised neurological hallmarks in the brain, which include the deposition of Aβ in parenchymal plaques and cerebral vessels, intraneuronal formation of neurofibrillary tangles, synaptic loss and loss of neuronal subpopulations in specific brain regions (Terry, R D (1991) J Neural Trans Suppl 53: 141-145).

A plethora of genetic, histological and functional evidence suggests that the β-amyloid peptide (Aβ) is key to the progression of Alzheimer's disease (Selkoe, D. J. (2001) Physiological Reviews 81: 741-766).

Aβ is known to be produced through the cleavage of the beta amyloid precursor protein (also known as APP) by an aspartyl protease enzyme known as BACE1 (also known as β-secretase, Asp2 or Memapsin-2) (De Strooper, B. and Konig, G. (1999) Nature 402: 471-472). In addition to the parenchymal and vascular deposition, soluble oligomeric forms of Aβ have been postulated to contribute to the onset of AD and they may affect neuronal function initially by impairing synaptic function (Lambert et. al. (1998) Proceedings of the National Academy of Science, U.S.A. 95: 6448-6453). Although insoluble amyloid plaques are found early in AD and in MCI, the levels of soluble Aβ aggregates (referred to as oligomers or Aβ-derived diffusible ligands (ADDLs) are also increased in these individuals, and soluble Aβ levels correlate better with neurofibrillary degeneration, and the loss of synaptic markers than do amyloid plaques (Naslund et. al. (2000) J Am Med Assoc 283: 1571-1577, Younkin, S. (2001) Nat. Med. 1: 8-19). The highly amyloidogenic Aβ42 and amino-terminally truncated forms Aβx-42 are the predominant species of Aβ found in both diffuse and senile plaques (Iwatsubo, T (1994) Neuron. 13:45-53, Gravina, S A (1995) J. Biol. Chem. 270:7013-7016) The relative levels of Aβ42 appear to be the key regulator of Aβ aggregation into amyloid plaques, indeed Aβ42 has been shown to aggregate more readily that other Aβ forms in vitro (Jarrett, J T (1993) Biochemistry. 32:4693-4697) and as such Aβ42 has been implicated as the initiating molecule in the pathogenesis of AD (Younkin S G, (1998) J. Physiol. (Paris). 92:289-292). Although Aβ42 is a minor product of APP metabolism, small shifts in it's production are associated with large effects on Aβ deposition therefore it has been postulated that reduction of Aβ42 alone may be an effective way of treating AD (Younkin S G, (1998) J. Physiol. (Paris). 92:289-292) In support of this, mutations in the amyloid precursor protein (APP) and presenilin genes have been reported to predominantly increase the relative levels of Aβ42 and therefore shortening the time to onset of Alzheimer's disease (AD) (Selkoe D. J., Podlisny M. B. (2002) Annu. Rev. Genomics Hum. Gemet. 3:67-99). It should be noted however, that the rate of deposition is also dependant on catabolism and Aβ clearance.

Animal models of amyloid deposition have been generated by overexpressing mutant human transgenes in mice. Mice overexpressing single human APP transgenes typically develop cerebral plaque-like β-amyloid deposits from 12 months of age (Games D. et al., (1995) Nature 373: 523-527; Hsiao K. et al., (1996) Science 274: 99-102)), while mice carrying both mutant human APP and presenilin-1 (PS-1) transgenes typically develop cerebral plaque-like β-amyloid deposits as early as 2 months of age (Kurt M. A. et al., (2001) Exp. Neurol. 171: 59-71; McGowan E. et al., (1999) Neurolbiol. Dis. 6: 231-244.

It has become increasingly apparent that the transport of exogenous Aβ between the central nervous system (CNS) and plasma plays a role in the regulation of brain amyloid levels (Shibata, et al (2000) J Clin Invest 106: 1489-1499), with CSF Aβ being rapidly transported from CSF to plasma. Therefore active vaccination with Aβ peptides or passive administration of specific Aβ antibodies rapidly binds peripheral Aβ altering the dynamic equilibrium between the plasma, CSF and ultimately the CNS. Indeed there are now a plethora of studies demonstrated both these approaches can lower Aβ levels, reduce Aβ pathology and provide cognitive benefit in various transgenic models of amyloidosis. Limited studies have also been conducted in higher species. Caribbean vervet monkeys (16-10 years old) were immunised with Aβ peptide over 10 months. Aβ40 levels were elevated 2-5 fold in the plasma which peaked at 251d while the CSF levels of Aβ40 and Aβ42 were significantly decreased by 100d and returned towards baseline thereafter. This reduction in CSF was accompanied by a significant reduction in plaque burden (Lemere, Calif. (2004) Am J Pathology 165: 283-297). Similar increases in plasma Aβ levels were also detected following immunisation of aged (15-20 year old) Rhesus Monkeys (Gandy, S (2004) Alzheimer Dis Assoc Disord 18: 44:46.

The first immune therapy targeting brain amyloid was Elan/Wyeth's AN-1792, an active vaccine. This treatment was terminated following the development of clinical signs consistent with meningoencephalitis. Subgroup analyses suggested that treatment slowed the decline of cognitive function (Nature Clin Pract Neurol (2005) 1:84-85). Post-mortem analysis of patients also showed evidence of plaque-clearance (Gilman S. et al, (2005) Neurology 64 (9) 1553-1562). Bapineuzumab (AAB-001, Elan/Wyeth), a passive MAb therapy has been shown to significantly improve cognition scores in a small phase I safety study.

Other diseases or disorders characterised by elevated β-amyloid levels or β-amyloid deposits include mild cognitive impairment (MCI, Blasko I (2006) Neurobiology of aging "Conversion from cognitive health to mild cognitive impairment and Alzheimer's disease: Prediction by plasma amyloid beta 42, medial temporal lobe atrophy and homocysteine" in press, e-published 19 Oct. 2006), hereditary cerebral haemorrhage with β-amyloidosis of the Dutch type, cerebral β-amyloid angiopathy and various types of degenerative dementias, such as those associated with Parkinson's disease, progressive supranuclear palsy, cortical basal degeneration and diffuse Lewis body type of Alzheimer's disease (Mollenhauer B (2007) J Neural Transm e-published 23 Feb. 2007, van Oijen, M Lancet Neurol. 2006 5:655-60) and Down syndrome (Mehta, PD (2007) J Neurol Sci. 254:22-7).

SUMMARY OF THE INVENTION

In an embodiment of the present invention there is provided a therapeutic antibody which is an antibody or antigen binding fragment and/or derivative thereof which binds β-amyloid peptide 1-12 (SEQ ID No:15) with equilibrium constant KD less than 100 pM but does not bind to β-amyloid peptide 2-13 (SEQ ID No:44), both determinations being made in a surface plasmon resonance assay utilising peptide captured on streptavidin chip.

In another embodiment of the present invention there is provided a therapeutic antibody which is an antibody or antigen binding fragment and/or derivative thereof which binds β-amyloid peptide 1-12 (SEQ ID No:15) with equilibrium constant KD less than 100 pM and has an equilibrium constant KD for binding to β-amyloid peptide 2-13 (SEQ ID No:44) which is 1000-fold greater than that for peptide 1-12 (SEQ ID No:15), both determinations being made in a surface plasmon resonance assay utilising peptide captured on streptavidin chip.

In another embodiment of the present invention there is provided a therapeutic antibody which is an antibody or antigen binding fragment and/or derivative thereof which binds β-amyloid peptide 1-12 (SEQ ID No:15) with equilibrium constant KD less than 100 pM and has an equilibrium constant KD for binding to β-amyloid peptide 2-13 (SEQ ID No:44) which is 10,000-fold greater than that for peptide 1-12 (SEQ ID No:15), both determinations being made in a surface plasmon resonance assay utilising peptide captured on streptavidin chip.

In one aspect the surface plasmon resonance assay utilising peptide captured on streptavidin chip is the Surface Plasmon Resonance assay described in the Example below. In another aspect the surface plasmon resonance assay utilising peptide captured on streptavidin chip is the Method A(i) described under SPR Biacore™ Analysis below.

In an alternative embodiment of the present invention there is provided a therapeutic antibody which is an antibody or antigen binding fragment and/or derivative thereof which binds β-amyloid peptide 1-40 with equilibrium constant KD less than 10 nM but does not bind to β-amyloid peptide 2-13 (SEQ ID No:44), both determinations being made in the surface plasmon resonance assay described in Method B of the Examples below.

In another alternative embodiment of the present invention there is provided a therapeutic antibody which is an antibody or antigen binding fragment and/or derivative thereof which binds β-amyloid peptide 1-40 with equilibrium constant KD less than 10 nM and has an equilibrium constant KD for binding to β-amyloid peptide 2-13 (SEQ ID No:44) which is 1000-fold greater than that for peptide 1-12 (SEQ ID No:15), both determinations being made in the surface plasmon resonance assay described in Method B of the Examples below.

In another alternative embodiment of the present invention there is provided a therapeutic antibody, which is an antibody or antigen binding fragment and/or derivative thereof which binds β-amyloid peptide 1-40 with equilibrium constant KD less than 10 nM and has an equilibrium constant KD for binding to β-amyloid peptide 2-13 (SEQ ID No:44) which is 10,000-fold greater than that for peptide 1-12 (SEQ ID No:15), both determinations being made in the surface plasmon resonance assay described in Method B of the Examples below.

In an embodiment of the present invention there is provided a therapeutic antibody which is an antibody or antigen binding fragment and/or derivative thereof which binds β-amyloid peptide and which comprises the following CDRs:
CDRH1: DNGMA (SEQ ID No:1)
CDRH2: FISNLAYSIDYADTVTG (SEQ ID No:2)
CDRH3: GTWFAY (SEQ ID No:3)
within a human heavy chain variable region originating from the VH3 gene family and:
CDRL1: RVSQSLLHSNGYTYLH (SEQ ID No:4)
CDRL2: KVSNRFS (SEQ ID No:5)
CDRL3: SQTRHVPYT (SEQ ID No:6)
within a human light chain variable region originating from the amino acid sequence disclosed in GenPept entry CAA51135 (SEQ ID No:24).

Throughout this specification, the terms "CDR", "CDRL1", "CDRL2", "CDRL3", "CDRH1", "CDRH2", "CDRH3" follow the Kabat numbering system as set forth in Kabat et al; *Sequences of proteins of Immunological Interest* NIH, 1987. Therefore the following defines the CDRs according to the invention:
CDR: Residues
CDRH1: 31-35B
CDRH2: 50-65
CDRH3: 95-102
CDRL1: 24-34
CDRL2: 50-56
CDRL3: 89-97

The VH3 gene family and related immunoglobulin gene nomenclature is described in Matsuda et al (Journal of Experimental Medicine, 188:2151-2162, 1998) and Lefranc & Lefranc (The Immunoglobulin Factsbook. 2001. Academic Press: London).

In a particular embodiment, the human heavy chain variable region originates from:
A V gene selected from the following subset of VH3 family members: VH3-48, VH3-21, VH3-11, VH3-7, VH3-13, VH3-74, VH3-64, VH3-23, VH3-38, VH3-53, VH3-66, VH3-20, VH3-9 & VH3-43
A V gene selected from the following subset of VH3 family members: VH3-48, VH3-21 & VH3-11
The VH3-48 gene
or an allele thereof.

The sequence in Genbank entry M99675 is an allele of the VH3-48 gene. M99675 is a Genbank nucleotide sequence of a genomic piece of DNA including the two exons that constitute the human heavy chain gene VH3-48 (SEQ ID No:22) and encode the variable region amino acid sequence given in SEQ ID No:21. In a particular aspect the human acceptor heavy chain framework is derived from M99675.

In order to construct a complete V-region a framework 4 has to be added to the germline encoded V-gene M99675. Suitable framework 4 sequences include that encoded by the human JH4 minigene (Kabat):
YFDYWGQGTLVTVSS (SEQ ID No:23)
of which the initial four residues fall within the CDR3 region which is replaced by the incoming CDR from the donor antibody.

The skilled person appreciates that a germline V gene and a J gene do not include coding sequence for the entirety of heavy chain CDR3. However, in the antibodies of the invention, the CDR3 sequence is provided by the donor immunoglobulin. Accordingly, the combination of a VH gene such as VH3-48, a JH minigene such as JH4, and a set of heavy chain CDRs, such as SEQ ID No:1, SEQ ID No:2 and SEQ ID No:3 (assembled in a manner so as to mimic a mature, fully rearranged heavy chain variable region) is sufficient to define a heavy chain variable region of the invention such as that represented in SEQ ID No:26, 28, 30.

The variable region encoded by Genpept ID CAA51134 has the amino acid sequence given in SEQ ID No:24.

The light chain variable region framework sequence known by the GenPept ID CAA51134 is the deduced amino acid sequence of a fully rearranged light chain variable region and is identical to another amino acid sequence with the same frameworks in the database: Genpept accession number S40356, and is described in Klein, R., et al., Eur. J. Immunol. 23 (12), 3248-3262 (1993). The DNA coding sequence for CAA51134, accessible as Genbank Accesion No X72467, is given as SEQ ID No: 25.

In a particular aspect of the invention the human acceptor heavy chain framework is derived from M99675 and the JH4 minigene and the human acceptor light chain framework is derived from CAA51135, optionally containing one or more, such as one to four, more particularly one to three, substitutions of amino acid residues based on the corresponding residues found in the donor $V_H$ domain having the sequence: SEQ ID No:17 and $V_L$ domain having the sequence: SEQ ID No: 19 that maintain all or substantially all of the binding affinity of the donor antibody for β-amyloid peptide.

By 'substantially all of the binding affinity' is meant that the therapeutic antibody has at most a ten-fold reduction in binding affinity compared to the donor antibody.

In a more particular aspect the human acceptor heavy chain framework derived from M99675 and JH4 has one to four amino acid residue substitutions selected from positions 24, 48, 93 and/or 94 (Kabat numbering).

In a more particular aspect of the invention the human acceptor heavy chain framework derived from M99675 and JH4 comprises the following residues (or a conservative substitute thereof):

| Position | Residue |
|---|---|
| (i) | |
| 93 | V |
| 94 | S |
| or (ii) | |
| 24 | V |
| 93 | V |
| 94 | S |
| or (iii) | |
| 48 | I |
| 93 | V |
| 94 | S |

In one embodiment of the invention there is provided a therapeutic antibody comprising a $V_H$ chain having the sequence set forth in SEQ ID No:26, 28 or 30 and a $V_L$ domain having the sequence set forth in SEQ ID No:32.

In another embodiment of the invention there is provided a therapeutic antibody, which antibody comprises a heavy chain having the sequence set forth in SEQ ID No:34, 36 or 38 and a light chain having the sequence set forth in SEQ ID No:40.

In another embodiment of the invention there is provided a pharmaceutical composition comprising a therapeutic antibody according to the invention.

In a further embodiment of the invention there is provided a method of treating a human patient afflicted with a β-amyloid peptide-related disease which method comprises the step of administering to said patient a therapeutically effective amount of a therapeutic antibody according to the invention.

Use of a therapeutic antibody according to the invention in the manufacture of a medicament for the treatment of a β-amyloid peptide-related disease is also provided.

In another embodiment of the invention there is provided a process for the manufacture of a therapeutic antibody according to the invention, which process comprises expressing polynucleotide encoding the antibody in a host cell.

In another embodiment of the invention there is provided a polynucleotide encoding a therapeutic antibody heavy chain comprising a $V_H$ chain having the sequence set forth in SEQ ID No:26, 28 or 30.

In another embodiment of the invention there is provided a polynucleotide encoding a therapeutic antibody light chain comprising a $V_L$ domain having the sequence set forth in SEQ ID No:32.

In another embodiment of the invention there is provided a polynucleotide encoding a therapeutic antibody heavy chain having the sequence set forth in SEQ ID No:34, 36 or 38.

In another embodiment of the invention there is provided a polynucleotide encoding a therapeutic antibody light chain having the sequence set forth in SEQ ID No:40.

In a more particular embodiment of the invention there is provided a polynucleotide encoding a therapeutic antibody heavy chain, which polynucleotide comprises the sequence set forth in SEQ ID No:35, 37, 39 or 42.

In another more particular embodiment of the invention there is provided a polynucleotide encoding a therapeutic antibody light chain, which polynucleotide comprises the sequence set forth in SEQ ID No:41 or 43.

In a particular embodiment the therapeutic antibody which is an antibody or fragment and/or derivative thereof essentially lacks the functions of a) activation of complement by the classical pathway; and b) mediating antibody-dependent cellular cytotoxicity.

In another embodiment of the invention there is provided an antibody or a fragment thereof comprising a $V_H$ domain having the sequence: SEQ ID No:17 and a V_L domain having the sequence: SEQ ID No: 19.

In another embodiment of the invention there is provided a polynucleotide encoding an antibody heavy chain or a fragment thereof comprising a V_H domain having the sequence SEQ ID No:17, in particular the polynucleotide of SEQ ID No:18.

In another embodiment of the invention there is provided a polynucleotide encoding an antibody light chain or a fragment thereof comprising a V_L domain having the sequence SEQ ID No: 19, in particular the polynucleotide of SEQ ID No:20.

DETAILED DESCRIPTION OF THE INVENTION

1. Antibody Structures
1.1 Intact Antibodies

Intact antibodies are usually heteromultimeric glycoproteins comprising at least two heavy and two light chains. Aside from IgM, intact antibodies are heterotetrameric glycoproteins of approximately 150 KDa, composed of two identical light (L) chains and two identical heavy (H) chains. Typically, each light chain is linked to a heavy chain by one covalent disulfide bond while the number of disulfide linkages between the heavy chains of different immunoglobulin isotypes varies. Each heavy and light chain also has intrachain disulfide bridges. Each heavy chain has at one end a variable domain ($V_H$) followed by a number of constant regions. Each light chain has a variable domain ($V_L$) and a constant region at its other end; the constant region of the light chain is aligned with the first constant region of the heavy chain and the light chain variable domain is aligned with the variable domain of the heavy chain. The light chains of antibodies from most vertebrate species can be assigned to one of two types called Kappa and Lambda based on the amino acid sequence of the constant region. Depending on the amino acid sequence of the constant region of their heavy chains, human antibodies can be assigned to five different classes, IgA, IgD, IgE, IgG and IgM. IgG and IgA can be further subdivided into subclasses, IgG1, IgG2, IgG3 and IgG4; and IgA1 and IgA2. Species variants exist with mouse and rat having at least IgG2a, IgG2b. The variable domain of the antibody confers binding specificity upon the antibody with certain regions displaying particular variability called complementarity determining regions (CDRs). The more conserved portions of the variable region are called framework regions (FR). The variable domains of intact heavy and light chains each comprise four FR connected by three CDRs. The CDRs in each chain are held together in close proximity by the FR regions and with the CDRs from the other chain contribute to the formation of the antigen binding site of antibodies. The constant regions are not directly involved in the binding of the antibody to the antigen but exhibit various effector functions such as participation in antibody dependent cell-mediated cytotoxicity (ADCC), phagocytosis via binding to Fcγ receptor, half-life/clearance rate via neonatal Fc receptor (FcRn) and complement dependent cytotoxicity via the C1q component of the complement cascade. The human IgG2 constant region lacks the ability to activate complement by the classical pathway or to mediate antibody-dependent cellular cytotoxicity. The IgG4 constant region lacks the ability to activate complement by the classical pathway and mediates antibody-dependent cellular cytotoxicity only weakly. Antibodies essentially lacking these effector functons may be termed 'non-lytic' antibodies.

1.1.1 Human Antibodies

Human antibodies may be produced by a number of methods known to those of skill in the art. Human antibodies can be made by the hybridoma method using human myeloma or mouse-human heteromyeloma cells lines see Kozbor J. Immunol 133, 3001, (1984) and Brodeur, Monoclonal Antibody Production Techniques and Applications, pp 51-63 (Marcel Dekker Inc, 1987). Alternative methods include the use of phage libraries or transgenic mice both of which utilize human V region repertories (see Winter G, (1994), Annu. Rev. Immunol 12,433-455, Green L L (1999), J. Immunol. methods 231, 11-23).

Several strains of transgenic mice are now available wherein their mouse immunoglobulin loci has been replaced with human immunoglobulin gene segments (see Tomizuka K, (2000) PNAS 97,722-727; Fishwild D. M (1996) Nature Biotechnol. 14,845-851, Mendez M J, 1997, Nature Genetics, 15,146-156). Upon antigen challenge such mice are capable of producing a repertoire of human antibodies from which antibodies of interest can be selected.

Of particular note is the Trimera™ system (see Eren R et al, (1998) Immunology 93:154-161) where human lymphocytes are transplanted into irradiated mice, the Selected Lymphocyte Antibody System (SLAM, see Babcook et al, PNAS (1996) 93:7843-7848) where human (or other species) lymphocytes are effectively put through a massive pooled in vitro antibody generation procedure followed by deconvulated, limiting dilution and selection procedure and the Xenomouse II™ (Abgenix Inc). An alternative approach is available from Morphotek Inc using the Morphodoma™ technology.

Phage display technology can be used to produce human antibodies (and fragments thereof), see McCafferty; Nature, 348, 552-553 (1990) and Griffiths A D et al (1994) EMBO 13:3245-3260. According to this technique antibody V domain genes are cloned in frame into either a major or minor coat of protein gene of a filamentous bacteriophage such as M13 or fd and displayed (usually with the aid of a helper phage) as functional antibody fragments on the surface of the phage particle. Selections based on the functional properties of the antibody result in selection of the gene encoding the antibody exhibiting those properties. The phage display technique can be used to select antigen specific antibodies from libraries made from human B cells taken from individuals afflicted with a disease or disorder described above or alternatively from unimmunized human donors (see Marks; J. Mol. Bio. 222,581-597, 1991). Where an intact human antibody is desired comprising a Fc domain it is necessary to reclone the phage displayed derived fragment into a mammalian expression vectors comprising the desired constant regions and establishing stable expressing cell lines.

The technique of affinity maturation (Marks; Bio/technol 10,779-783 (1992)) may be used to improve binding affinity wherein the affinity of the primary human antibody is improved by sequentially replacing the H and L chain V regions with naturally occurring variants and selecting on the basis of improved binding affinities. Variants of this technique such as "epitope imprinting" are now also available see WO 93/06213. See also Waterhouse; Nucl. Acids Res 21, 2265-2266 (1993).

1.2 Chimaeric and Humanised Antibodies

The use of intact non-human antibodies in the treatment of human diseases or disorders carries with it the now well established problems of potential immunogenicity especially upon repeated administration of the antibody that is the immune system of the patient may recognise the non-human intact antibody as non-self and mount a neutralising response. In addition to developing fully human antibodies (see above)

various techniques have been developed over the years to overcome these problems and generally involve reducing the composition of non-human amino acid sequences in the intact therapeutic antibody whilst retaining the relative ease in obtaining non-human antibodies from an immunised animal e.g. mouse, rat or rabbit. Broadly two approaches have been used to achieve this. The first are chimaeric antibodies, which generally comprise a non-human (e.g. rodent such as mouse) variable domain fused to a human constant region. Because the antigen-binding site of an antibody is localised within the variable regions the chimaeric antibody retains its binding affinity for the antigen but acquires the effector functions of the human constant region and are therefore able to perform effector functions such as described supra. Chimaeric antibodies are typically produced using recombinant DNA methods. DNA encoding the antibodies (e.g. cDNA) is isolated and sequenced using conventional procedures (e.g. by using oligonucleotide probes that are capable of binding specifically to genes encoding the H and L chain variable regions of the antibody of the invention, e.g. DNA of SEQ.I.D.NO 18 and 20 described supra). Hybridoma cells serve as a typical source of such DNA. Once isolated, the DNA is placed into expression vectors which are then transfected into host cells such as *E.Coli*, COS cells, CHO cells, PerC6 cells or myeloma cells that do not otherwise produce immunoglobulin protein to obtain synthesis of the antibody. The DNA may be modified by substituting the coding sequence for human L and H chains for the corresponding non-human (e.g. murine) H and L constant regions see e.g. Morrison; PNAS 81, 6851 (1984). Thus another embodiment of the invention there is provided a chimaeric antibody comprising a $V_H$ domain having the sequence: SEQ ID No:17 and a $V_L$ domain having the sequence: SEQ ID No: 19 fused to a human constant region (which maybe of a IgG isotype e.g. IgG1).

The second approach involves the generation of humanised antibodies wherein the non-human content of the antibody is reduced by humanizing the variable regions.

Two techniques for humanisation have gained popularity. The first is humanisation by CDR grafting. CDRs build loops close to the antibody's N-terminus where they form a surface mounted in a scaffold provided by the framework regions. Antigen-binding specificity of the antibody is mainly defined by the topography and by the chemical characteristics of its CDR surface. These features are in turn determined by the conformation of the individual CDRs, by the relative disposition of the CDRs, and by the nature and disposition of the side chains of the residues comprising the CDRs. A large decrease in immunogenicity can be achieved by grafting only the CDRs of a non-human (e.g. murine) antibodies ("donor" antibodies) onto a suitable human framework ("acceptor framework") and constant regions (see Jones et al (1986) Nature 321,522-525 and Verhoeyen M et al (1988) Science 239, 1534-1536). However, CDR grafting per se may not result in the complete retention of antigen-binding properties and it is frequently found that some framework residues of the donor antibody need to be preserved (sometimes referred to as "backmutations") in the humanised molecule if significant antigen-binding affinity is to be recovered (see Queen C et al (1989) PNAS 86, 10,029-10,033, Co, M et al (1991) Nature 351, 501-502). In this case, human V regions showing the greatest sequence homology (typically 60% or greater) to the non-human donor antibody maybe chosen from a database in order to provide the human framework (FR). The selection of human FRs can be made either from human consensus or individual human antibodies. Where necessary key residues from the donor antibody are substituted into the human acceptor framework to preserve CDR conformations. Computer modelling of the antibody maybe used to help identify such structurally important residues, see WO99/48523.

Alternatively, humanisation maybe achieved by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan E. A. et al; (1991) Mol. Immunol.28, 489-498 and Pedersen J. T. et al (1994) J. Mol. Biol. 235; 959-973). Therefore it is possible to reduce the immunogenicity of a non-human Fv by replacing exposed residues in its framework regions that differ from those usually found in human antibodies. Because protein antigenicity can be correlated with surface accessibility, replacement of the surface residues may be sufficient to render the mouse variable region "invisible" to the human immune system (see also Mark G. E. et al (1994) in *Handbook of Experimental Pharmacology vol.* 113: *The pharmacology of monoclonal Antibodies*, Springer-Verlag, pp105-134). This procedure of humanisation is referred to as "veneering" because only the surface of the antibody is altered, the supporting residues remain undisturbed. Further alternative approaches include that set out in WO04/006955 and the procedure of Humaneering™ (Kalobios) which makes use of bacterial expression systems and produces antibodies that are close to human germline in sequence (Alfenito-M Advancing Protein Therapeutics January 2007, San Diego, Calif.).

It will be apparent to those skilled in the art that the term "derived" is intended to define not only the source in the sense of it being the physical origin for the material but also to define material which is structurally identical to the material but which does not originate from the reference source. Thus "residues found in the donor antibody" need not necessarily have been purified from the donor antibody.

It is well recognised in the art that certain amino acid substitutions are regarded as being "conservative". Amino acids are divided into groups based on common side-chain properties and substitutions within groups that maintain all or substantially all of the binding affinity of the therapeutic antibody of the invention are regarded as conservative substitutions, see the following Table 1:

TABLE 1

| Side chain | Members |
| --- | --- |
| Hydrophobic | met, ala, val, leu, ile |
| neutral hydrophilic | cys, ser, thr |
| Acidic | asp, glu |
| Basic | asn, gln, his, lys, arg |
| residues that influence chain orientation | gly, pro |
| aromatic | trp, tyr, phe |

1.3 Bispecific Antibodies

A bispecific antibody is an antibody derivative having binding specificities for at least two different epitopes and also forms part of the invention. Methods of making such antibodies are known in the art. Traditionally, the recombinant production of bispecific antibodies is based on the coexpression of two immunoglobulin H chain-L chain pairs, where the two H chains have different binding specificities see Millstein et al, Nature 305 537-539 (1983), WO93/08829 and Traunecker et al EMBO, 10, 1991, 3655-3659. Because of the random assortment of H and L chains, a potential mixture of ten different antibody structures are produced of which only one has the desired binding specificity. An alternative approach involves fusing the variable domains with the desired binding specificities to heavy chain constant region comprising at least part of the hinge region, CH2 and CH3 regions. It is preferred to have the CH1 region containing the site necessary for light chain binding present in at least one of the fusions. DNA encoding these fusions, and if desired the L chain are inserted into separate expression vectors and are then cotransfected into a suitable host organism. It is possible though to insert the coding sequences for two or all three chains into one expression vector. In one preferred approach, the bispecific antibody is composed of a H chain with a first binding specificity in one arm and a H-L chain pair, providing a second binding specificity in the other arm, see WO94/04690. See also Suresh et al Methods in Enzymology 121, 210, 1986.

Delivery of therapeutic proteins to the brain has been hampered by the presence of the blood brain barrier (BBB). Where it is desired to deliver an antibody of the invention or antibody fragment of the invention across the BBB various strategies have been proposed to enhance such delivery where needed.

In order to obtain required nutrients and factors from the blood, the BBB posseses some specific receptors, which transport compounds from the circulating blood to the brain. Studies have indicated that some compounds like insulin (see Duffy K R et al (1989) Brain Res. 420:32-38), transferin (see Fishman J B et al (1987) J. Neurosci 18:299-304) and insulin like growth factors 1 and 2 (see Pardridge W M (1986) Endocrine Rev. 7:314-330 and Duffy K R et al (1986) Metabolism 37:136-140) traverse the BBB via receptor-mediated transcytosis. Receptors for these molecules thus provide a potential means for therapeutic antibodies of the invention to access the brain using so-called "vectored" antibodies (see Pardridge W M (1999) Advanced Drug Delivery Review 36:299-321). For example, an antibody to transferrin receptor has been shown to be dynamically transported into the brain parenchyma (see Friden P M et al (1991) PNAS 88:4771-4775 and Friden P M et al (1993) Science 259:373-377). Thus one potential approach is to produce a bispecific antibody or bispecific fragment such as described supra wherein a first specificity is towards and a second specificity towards a transport receptor located at the BBB e.g. a second specificity towards the transferrin transport receptor.

1.4 Antibody Fragments

In certain embodiments of the invention there is provided therapeutic antibody which is an antigen binding fragment. Such fragments may be functional antigen binding fragments of intact and/or humanised and/or chimaeric antibodies such as Fab, Fd, Fab', F(ab')$_2$, Fv, ScFv fragments of the antibodies described supra. Fragments lacking the constant region lack the ability to activate complement by the classical pathway or to mediate antibody-dependent cellular cytotoxicity. Traditionally such fragments are produced by the proteolytic digestion of intact antibodies by e.g. papain digestion (see for example, WO 94/29348) but may be produced directly from recombinantly transformed host cells. For the production of ScFv, see Bird at al; (1988) Science, 242, 423-426. In addition, antibody fragments may be produced using a variety of engineering techniques as described below.

Fv fragments appear to have lower interaction energy of their two chains than Fab fragments. To stablise the association of the $V_H$ and $V_L$ domains, they have been linked with peptides (Bird et al, (1988) Science 242, 423-426, Huston et al, PNAS, 85, 5879-5883), disulphide bridges (Glockshuber et al, (1990) Biochemistry, 29, 1362-1367) and "knob in hole" mutations (Zhu et al (1997), Protein Sci., 6, 781-788). ScFv fragments can be produced by methods well known to those skilled in the art see Whitlow et al (1991) Methods companion Methods Enzymol, 2, 97-105 and Huston et al (1993) Int.Rev.Immunol 10, 195-217. ScFv may be produced in bacterial cells such as E.Coli but are more typically produced in eukaryotic cells. One disadvantage of ScFv is the monovalency of the product, which precludes an increased avidity due to polyvalent binding, and their short half-life. Attempts to overcome these problems include bivalent (ScFv')$_2$ produced from ScFV containing an additional C terminal cysteine by chemical coupling (Adams at al (1993) Can. Res 53, 4026-4034 and McCartney et al (1995) Protein Eng. 8, 301-314) or by spontaneous site-specific dimerization of ScFv containing an unpaired C terminal cysteine residue (see Kipriyanov at al (1995) Cell. Biophys 26, 187-204). Alternatively, ScFv can be forced to form multimers by shortening the peptide linker to between 3 to 12 residues to form "diabodies", see Holliger at al PNAS (1993), 90, 6444-6448. Reducing the linker still further can result in ScFV trimers ("triabodies", see Kortt et al (1997) Protein Eng, 10, 423-433) and tetramers ("tetrabodies", see Le Gall et al (1999) FEBS Lett, 453, 164-168). Construction of bivalent ScFV molecules can also be achieved by genetic fusion with protein dimerizing motifs to form "miniantibodies" (see Pack et al (1992) Biochemistry 31, 1579-1584) and "minibodies" (see Hu et al (1996), Cancer Res. 56, 3055-3061). ScFv-Sc-Fv tandems ((ScFV)$_2$) may also be produced by linking two ScFv units by a third peptide linker, see Kurucz et al (1995) J. Immol. 154, 4576-4582. Bispecific diabodies can be produced through the noncovalent association of two single chain fusion products consisting of $V_H$ domain from one antibody connected by a short linker to the $V_L$ domain of another antibody, see Kipriyanov et al (1998), Int. J. Can 77,763-772. The stability of such bispecific diabodies can be enhanced by the introduction of disulphide bridges or "knob in hole" mutations as described supra or by the formation of single chain diabodies (ScDb) wherein two hybrid ScFv fragments are connected through a peptide linker see Kontermann et al (1999) J. Immunol. Methods 226 179-188. Tetravalent bispecific molecules are available by e.g. fusing a ScFv fragment to the CH3 domain of an IgG molecule or to a Fab fragment through the hinge region see Coloma et al (1997) Nature Biotechnol. 15, 159-163. Alternatively, tetravalent bispecific molecules have been created by the fusion of bispecific single chain diabodies (see Alt et al, (1999) FEBS Lett 454, 90-94. Smaller tetravalent bispecific molecules can also be formed by the dimerization of either ScFv-ScFv tandems with a linker containing a helix-loop-helix motif (DiBi miniantibodies, see Muller et al (1998) FEBS Lett 432, 45-49) or a single chain molecule comprising four antibody variable domains ($V_H$ and $V_L$) in an orientation preventing intramolecular pairing (tandem diabody, see Kipriyanov et al, (1999) J. Mol. Biol. 293, 41-56). Bispecific F(ab')2 fragments can be created by chemical coupling of Fab' fragments or by heterodimerization through leucine zippers (see Shalaby et al, (1992) J. Exp. Med. 175, 217-225 and Kostelny et al (1992), J. Immunol. 148, 1547-1553). Also available are isolated $V_H$ and $V_L$ domains, see U.S. Pat. No. 6, 248,516; U.S. Pat. No. 6,291,158; U.S. Pat. No. 6,172,197.

1.5 Heteroconjugate Antibodies

Heteroconjugate antibodies are derivatives which also form an embodiment of the present invention. Heteroconjugate antibodies are composed of two covalently joined antibodies formed using any convenient cross-linking methods. See U.S. Pat. No. 4,676,980.

1.6 Other Modifications.

The interaction between the Fc region of an antibody and various Fc receptors (FcγR) is believed to mediate the effector functions of the antibody which include antibody-dependent cellular cytotoxicity (ADCC), fixation of complement, phagocytosis and half-life/clearance of the antibody. Various modifications to the Fc region of antibodies of the invention may be carried out depending on the desired effector property. In particular, human constant regions which essentially lack the functions of a) activation of complement by the classical pathway; and b) mediating antibody-dependent cellular cytotoxicity include the IgG4 constant region, the IgG2 constant region and IgG1 constant regions containing specific mutations as for example mutations at positions 234, 235, 236, 237, 297, 318, 320 and/or 322 disclosed in EP0307434 (WO8807089), EP 0629 240 (WO9317105) and WO 2004/014953. Mutations at residues 235 or 237 within the CH2 domain of the heavy chain constant region (Kabat numbering; EU Index system) have separately been described to reduce binding to FcγRI, FcγRII and FcγRIII binding and therefore reduce antibody-dependent cellular cytotoxicity (ADCC) (Duncan et al. Nature 1988, 332; 563-564; Lund et al. J. Immunol. 1991, 147; 2657-2662; Chappel et al. PNAS 1991, 88; 9036-9040; Burton and Woof, Adv. Immunol. 1992, 51;1-84; Morgan et al., Immunology 1995, 86; 319-324; Hezareh et al., J. Virol. 2001, 75 (24); 12161-12168). Further, some reports have also described involvement of some of these residues in recruiting or mediating complement dependent cytotoxicity (CDC) (Morgan et al., 1995; Xu et al., Cell. Immunol. 2000; 200:16-26; Hezareh et al., J. Virol. 2001, 75 (24); 12161-12168). Residues 235 and 237 have therefore both been mutated to alanine residues (Brett et al. Immunology 1997, 91; 346-353; Bartholomew et al. Immunology 1995, 85; 41-48; and WO9958679) to reduce both complement mediated and FcγR-mediated effects. Antibodies comprising these constant regions may be termed 'non-lytic' antibodies.

One may incorporate a salvage receptor binding epitope into the antibody to increase serum half life see U.S. Pat. No. 5,739,277.

There are five currently recognised human Fcγ receptors, FcγR (I), FcγRIIa, FcγRIIb, FcγRIIIa and neonatal FcRn. Shields et al, (2001) J. Biol. Chem 276, 6591-6604 demonstrated that a common set of IgG1 residues is involved in binding all FcγRs, while FcγRII and FcγRIII utilize distinct sites outside of this common set. One group of IgG1 residues reduced binding to all FcγRs when altered to alanine: Pro-238, Asp-265, Asp-270, Asn-297 and Pro-239. All are in the IgG CH2 domain and clustered near the hinge joining CH1 and CH2. While FcγRI utilizes only the common set of IgG1 residues for binding, FcγRII and FcγRIII interact with distinct residues in addition to the common set. Alteration of some residues reduced binding only to FcγRII (e.g. Arg-292) or FcγRIII (e.g. Glu-293). Some variants showed improved binding to FcγRII or FcγRIII but did not affect binding to the other receptor (e.g. Ser-267Ala improved binding to FcγRII but binding to FcγRIII was unaffected). Other variants exhibited improved binding to FcγRII or FcγRIII with reduction in binding to the other receptor (e.g. Ser-298Ala improved binding to FcγRIII and reduced binding to FcγRII). For FcγRIIIa, the best binding IgG1 variants had combined alanine substitutions at Ser-298, Glu-333 and Lys-334. The neonatal FcRn receptor is believed to be involved in protecting IgG molecules from degradation and thus enhancing serum half life and the transcytosis across tissues (see Junghans R. P (1997) Immunol. Res 16. 29-57 and Ghetie et al (2000) Annu. Rev. Immunol. 18, 739-766). Human IgG1 residues determined to interact directly with human FcRn includes Ile253, Ser254, Lys288, Thr307, Gln311, Asn434 and His435.

The therapeutic antibody of the invention may incorporate any of the above constant region modifications.

In a particular embodiment, the therapeutic antibody essentially lacks the functions of a) activation of complement by the classical pathway; and b) mediating antibody-dependent cellular cytotoxicity. In a more particular embodiment the present invention provides therapeutic antibodies of the invention having any one (or more) of the residue changes detailed above to modify half-life/clearance and/or effector functions such as ADCC and/or complement dependent cytotoxicity and/or complement lysis.

In a further aspect of the present invention the therapeutic antibody has a constant region of isotype human IgG1 with alanine (or other disrupting) substitutions at positions 235 (e.g. L235A) and 237 (e.g. G237A) (numbering according to the EU scheme outlined in Kabat.

Other derivatives of the invention include glycosylation variants of the antibodies of the invention. Glycosylation of antibodies at conserved positions in their constant regions is known to have a profound effect on antibody function, particularly effector functioning such as those described above, see for example, Boyd et al (1996), Mol. Immunol. 32, 1311-1318. Glycosylation variants of the therapeutic antibodies of the present invention wherein one or more carbohydrate moiety is added, substituted, deleted or modified are contemplated. Introduction of an asparagine-X-serine or asparagine-X-threonine motif creates a potential site for enzymatic attachment of carbohydrate moieties and may therefore be used to manipulate the glycosylation of an antibody. In Raju et al (2001) Biochemistry 40, 8868-8876 the terminal sialyation of a TNFR-IgG immunoadhesin was increased through a process of regalactosylation and/or resialylation using beta-1,4-galactosyltransferace and/or alpha, 2,3 sialyltransferase. Increasing the terminal sialylation is believed to increase the half-life of the immunoglobulin. Antibodies, in common with most glycoproteins, are typically produced in nature as a mixture of glycoforms. This mixture is particularly apparent when antibodies are produced in eukaryotic, particularly mammalian cells. A variety of methods have been developed to manufacture defined glycoforms, see Zhang et al Science (2004), 303, 371, Sears et al, Science, (2001) 291, 2344, Wacker et al (2002) Science, 298 1790, Davis et al (2002) Chem. Rev. 102, 579, Hang et al (2001) Acc. Chem. Res 34, 727. Thus the invention concerns a plurality of therapeutic antibodies (which maybe of the IgG isotype, e.g. IgG1) as described herein comprising a defined number (e.g. 7 or less, for example 5 or less such as two or a single) glycoform(s) of said antibodies.

Derivatives according to the invention also include therapeutic antibodies of the invention coupled to a non-proteinaceous polymer such as polyethylene glycol (PEG), polypropylene glycol or polyoxyalkylene. Conjugation of proteins to PEG is an established technique for increasing half-life of proteins, as well as reducing antigenicity and immunogenicity of proteins. The use of PEGylation with different molecular weights and styles (linear or branched) has been investigated with intact antibodies as well as Fab' fragments, see Koumenis I. L. et al (2000) Int. J. Pharmaceut. 198:83-95. A particular embodiment comprises an antigen-binding fragment of the invention without the effector functions of a) activation of complement by the classical pathway; and b) mediating antibody-dependent cellular cytotoxicity; (such as a Fab fragment or a scFv) coupled to PEG.

2. Production Methods

Antibodies of the present invention may be produced in transgenic organisms such as goats (see Pollock et al (1999), J. Immunol. Methods 231:147-157), chickens (see Morrow K J J (2000) Genet. Eng. News 20:1-55), mice (see Pollock et al ibid) or plants (see Doran P M, (2000) Curr. Opinion Biotechnol. 11, 199-204, Ma J K-C (1998), Nat. Med. 4; 601-606, Baez J et al, BioPharm (2000) 13: 50-54, Stoger E et al; (2000) Plant Mol. Biol. 42:583-590). Antibodies may also be produced by chemical synthesis. However, antibodies of the invention are typically produced using recombinant cell culturing technology well known to those skilled in the art. A polynucleotide encoding the antibody is isolated and inserted into a replicable vector such as a plasmid for further propagation or expression in a host cell. One useful expression system is a glutamate synthetase system (such as sold by Lonza Biologics), particularly where the host cell is CHO or NSO (see below). Polynucleotide encoding the antibody is readily isolated and sequenced using conventional procedures (e.g. oligonucleotide probes). Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotide encoding the light and heavy chains may be inserted into separate vectors and introduced (e.g. by transformation, transfection, electroporation or transduction) into the same host cell concurrently or sequentially or, if desired both the heavy chain and light chain can be inserted into the same vector prior to such introduction.

It will be immediately apparent to those skilled in the art that due to the redundancy of the genetic code, alternative polynucleotides to those disclosed herein are also available that will encode the polypeptides of the invention.

2.1 Signal Sequences

Antibodies of the present invention maybe produced as a fusion protein with a heterologous signal sequence having a specific cleavage site at the N terminus of the mature protein. The signal sequence should be recognised and processed by the host cell. For prokaryotic host cells, the signal sequence may be an alkaline phosphatase, penicillinase, or heat stable enterotoxin II leaders. For yeast secretion the signal sequences may be a yeast invertase leader, a factor leader or acid phosphatase leaders see e.g. WO90/13646. In mammalian cell systems, viral secretory leaders such as herpes simplex gD signal and native immunoglobulin signal sequences (such as human Ig heavy chain) are available. Typically the signal sequence is ligated in reading frame to polynucleotide encoding the antibody of the invention.

2.2 Origin of Replication

Origin of replications are well known in the art with pBR322 suitable for most gram-negative bacteria, 2µ. plasmid for most yeast and various viral origins such as SV40, polyoma, adenovirus, VSV or BPV for most mammalian cells. Generally the SV40 origin of replication component is not needed for integrated mammalian expression vectors. However the SV40 on may be included since it contains the early promoter.

2.3 Selection Marker

Typical selection genes encode proteins that (a) confer resistance to antibiotics or other toxins e.g. ampicillin, neomycin, methotrexate or tetracycline or (b) complement auxotrophic deficiencies or supply nutrients not available in the complex media or (c) combinations of both. The selection scheme may involve arresting growth of the host cells that contain no vector or vectors. Cells, which have been successfully transformed with the genes encoding the therapeutic antibody of the present invention, survive due to e.g. drug resistance conferred by the co-delivered selection marker. One example is the DHFR-selection system wherein transformants are generated in DHFR negative host strains (eg see Page and Sydenham 1991 Biotechnology 9: 64-68). In this system the DHFR gene is co-delivered with antibody polynucleotide sequences of the invention and DHFR positive cells then selected by nucleoside withdrawal. If required, the DHFR inhibitor methotrexate is also employed to select for transformants with DHFR gene amplification. By operably linking DHFR gene to the antibody coding sequences of the invention or functional derivatives thereof, DHFR gene amplification results in concomitant amplification of the desired antibody sequences of interest. CHO cells are a particularly useful cell line for this DHFR/methotrexate selection and methods of amplifying and selecting host cells using the DHFR system are well established in the art see Kaufman R. J. et al J. Mol. Biol. (1982) 159, 601-621, for review, see Werner R G, Noe W, Kopp K, Schluter M," Appropriate mammalian expression systems for biopharmaceuticals", Arzneimittel-Forschung. 48(8):870-80, 1998 August. A further example is the glutamate synthetase expression system (Bebbington et al Biotechnology 1992 Vol 10 p 169). A suitable selection gene for use in yeast is the trp1 gene; see Stinchcomb et al Nature 282, 38, 1979.

2.4 Promoters

Suitable promoters for expressing antibodies of the invention are operably linked to DNA/polynucleotide encoding the antibody. Promoters for prokaryotic hosts include phoA promoter, Beta-lactamase and lactose promoter systems, alkaline phosphatase, tryptophan and hybrid promoters such as Tac. Promoters suitable for expression in yeast cells include 3-phosphoglycerate kinase or other glycolytic enzymes e.g. enolase, glyceralderhyde 3 phosphate dehydrogenase, hexokinase, pyruvate decarboxylase, phosphofructokinase, glucose 6 phosphate isomerase, 3-phosphoglycerate mutase and glucokinase. Inducible yeast promoters include alcohol dehydrogenase 2, isocytochrome C, acid phosphatase, metallothionein and enzymes responsible for nitrogen metabolism or maltose/galactose utilization. Promoters for expression in mammalian cell systems include RNA polymerase II promoters including viral promoters such as polyoma, fowlpox and adenoviruses (e.g. adenovirus 2), bovine papilloma virus, avian sarcoma virus, cytomegalovirus (in particular the immediate early gene promoter), retrovirus, hepatitis B virus, actin, rous sarcoma virus (RSV) promoter and the early or late Simian virus 40 and non-viral promoters such as EF-1alpha (Mizushima and Nagata Nucleic Acids Res 1990 18(17): 5322. The choice of promoter may be based upon suitable compatibility with the host cell used for expression.

2.5 Enhancer Element

Where appropriate, e.g. for expression in higher eukaroytics, additional enhancer elements can included instead of or as well as those found located in the promoters described above. Suitable mammalian enhancer sequences include enhancer elements from globin, elastase, albumin, fetoprotein, metallothionine and insulin. Alternatively, one may use an enhancer element from a eukaroytic cell virus such as SV40 enhancer, cytomegalovirus early promoter enhancer, polyoma enhancer, baculoviral enhancer or murine IgG2a locus (see WO04/009823). Whilst such enhancers are typically located on the vector at a site upstream to the promoter, they can also be located elsewhere e.g. within the untranslated region or downstream of the polydenalytion signal. The choice and positioning of enhancer may be based upon suitable compatibility with the host cell used for expression.

2.6 Polyadenylation/Termination

In eukaryotic systems, polyadenylation signals are operably linked to polynucleotide encoding the antibody of this invention. Such signals are typically placed 3' of the open reading frame. In mammalian systems, non-limiting example signals include those derived from growth hormones, elongation factor-1 alpha and viral (eg SV40) genes or retroviral long terminal repeats. In yeast systems non-limiting examples of polydenylation/termination signals include those derived from the phosphoglycerate kinase (PGK) and the alcohol dehydrogenase 1 (ADH) genes. In prokaryotic system polyadenylation signals are typically not required and it is instead usual to employ shorter and more defined terminator sequences. The choice of polyadenylation/termination sequences may be based upon suitable compatibility with the host cell used for expression.

2.7 Other Methods/Elements for Enhanced Yields

In addition to the above, other features that can be employed to enhance yields include chromatin remodelling elements, introns and host-cell specific codon modification. The codon useage of the antibody of this invention thereof can be modified to accommodate codon bias of the host cell such to augment transcript and/or product yield (eg Hoekema A et al Mol Cell Biol 1987 7(8):2914-24). The choice of codons may be based upon suitable compatibility with the host cell used for expression.

2.8 Host Cells

Suitable host cells for cloning or expressing vectors encoding antibodies of the invention are prokaroytic, yeast or higher eukaryotic cells. Suitable prokaryotic cells include eubacteria e.g. enterobacteriaceae such as Escherichia e.g. *E.Coli* (for example ATCC 31,446; 31,537; 27,325), *Enterobacter, Erwinia, Klebsiella Proteus, Salmonella* e.g. *Salmonella typhimurium, Serratia* e.g. *Serratia marcescans* and *Shigella* as well as *Bacilli* such as *B.subtilis* and *B.licheniformis* (see DD 266 710), *Pseudomonas* such as *P.aeruginosa* and *Streptomyces*. Of the yeast host cells, *Saccharomyces cerevisiae, schizosaccharomyces pombe, Kluyveromyces* (e.g. ATCC 16,045; 12,424; 24178; 56,500), yarrowia (EP402, 226), *Pichia Pastoris* (EP183, 070, see also Peng et al J.Biotechnol. 108 (2004) 185-192), *Candida, Trichoderma reesia* (EP244, 234), *Penicillin, Tolypocladium* and *Aspergillus* hosts such as *A.nidulans* and *A.niger* are also contemplated.

Although Prokaryotic and yeast host cells are specifically contemplated by the invention, typically however, host cells of the present invention are vertebrate cells. Suitable vertebrate host cells include mammalian cells such as COS-1 (ATCC No.CRL 1650) COS-7 (ATCC CRL 1651), human embryonic kidney line 293, PerC6 (Crucell), baby hamster kidney cells (BHK) (ATCC CRL.1632), BHK570 (ATCC NO: CRL 10314), 293 (ATCC NO.CRL 1573), Chinese hamster ovary cells CHO (e.g. CHO-K1, ATCC NO: CCL 61, DHFR minus CHO cell line such as DG44 (Urlaub et al, Somat Cell Mol Genet (1986) Vol 12 pp 555-566), particularly those CHO cell lines adapted for suspension culture, mouse sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells e.g. NSO (see U.S. Pat. No. 5,807,715), Sp2/0, Y0.

Thus in one embodiment of the invention there is provided a stably transformed host cell comprising a vector encoding a heavy chain and/or light chain of the therapeutic antibody as described herein. Typically such host cells comprise a first vector encoding the light chain and a second vector encoding said heavy chain.

Such host cells may also be further engineered or adapted to modify quality, function and/or yield of the antibody of this invention. Non-limiting examples include expression of specific modifiying (eg glycosylation) enzymes and protein folding chaperones.

2.9 Cell Culturing Methods.

Host cells transformed with vectors encoding the therapeutic antibodies of the invention may be cultured by any method known to those skilled in the art. Host cells may be cultured in spinner flasks, shake flasks, roller bottles, wave reactors (eg System 1000 from wavebiotech.com) or hollow fibre systems but it is preferred for large scale production that stirred tank reactors or bag reactors (eg Wave Biotech, Somerset, N.J. USA) are used particularly for suspension cultures. Typically the stirred tankers are adapted for aeration using e.g. spargers, baffles or low shear impellers. For bubble columns and airlift reactors direct aeration with air or oxygen bubbles maybe used. Where the host cells are cultured in a serum free culture media this can be supplemented with a cell protective agent such as pluronic F-68 to help prevent cell damage as a result of the aeration process. Depending on the host cell characteristics, either microcarriers maybe used as growth substrates for anchorage dependent cell lines or the cells maybe adapted to suspension culture (which is typical). The culturing of host cells, particularly vertebrate host cells may utilise a variety of operational modes such as batch, fed-batch, repeated batch processing (see Drapeau et al (1994) cytotechnology 15: 103-109), extended batch process or perfusion culture. Although recombinantly transformed mammalian host cells may be cultured in serum-containing media such media comprising fetal calf serum (FCS), it is preferred that such host cells are cultured in serum-free media such as disclosed in Keen et al (1995) Cytotechnology 17:153-163, or commercially available media such as ProCHO-CDM or UltraCHOTM (Cambrex N.J., USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g. Scharfenberg K et al (1995) in *Animal Cell technology: Developments towards the 21st century* (Beuvery E. C. et al eds), pp 619-623, Kluwer Academic publishers).

Antibodies of the invention secreted into the media may be recovered and purified from the media using a variety of techniques to provide a degree of purification suitable for the intended use. For example the use of therapeutic antibodies of the invention for the treatment of human patients typically mandates at least 95% purity as determined by reducing SDS-PAGE, more typically 98% or 99% purity, when compared to the culture media comprising the therapeutic antibodies. In the first instance, cell debris from the culture media is typically removed using centrifugation followed by a clarification step of the supernatant using e.g. microfiltration, ultrafiltration and/or depth filtration. Alternatively, the antibody can be harvested by microfiltration, ultrafiltration or depth filtration without prior centrifugation. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429,746) are available. In one embodiment, the antibodies of the invention, following various clarification steps, are captured using Protein A or G affinity chromatography followed by further chromatography steps such as ion exchange and/or HA chromatography, anion or cation exchange, size exclusion chromatography and ammonium sulphate precipitation. Typically, various virus removal steps are also employed (e.g. nanofiltration using e.g. a DV-20 filter). Following these various steps, a purified (typically monoclonal) preparation comprising at least 10 mg/ml or greater e.g. 100 mg/ml or greater of the antibody of the invention is provided and therefore forms an embodiment of the invention.

Concentration to 100 mg/ml or greater can be generated by ultracentrifugation. Suitably such preparations are substantially free of aggregated forms of antibodies of the invention.

Bacterial systems are particularly suited for the expression of antibody fragments. Such fragments are localised intracellularly or within the peripiasma. Insoluble periplasmic proteins can be extracted and refolded to form active proteins according to methods known to those skilled in the art, see Sanchez et al (1999) J.Biotechnol. 72, 13-20 and Cupit P M et al (1999) Lett Appl Microbiol, 29, 273-277.

3. Pharmaceutical Compositions

Purified preparations of antibodies of the invention (particularly monoclonal preparations) as described supra, may be incorporated into pharmaceutical compositions for use in the treatment of human diseases and disorders such as those outlined above. Typically such compositions further comprise a pharmaceutically acceptable (i.e. inert) carrier as known and called for by acceptable pharmaceutical practice, see e.g. Remingtons Pharmaceutical Sciences, 16th ed, (1980), Mack Publishing Co. Examples of such carriers include sterilised carrier such as saline, Ringers solution or dextrose solution, buffered with suitable buffers such as sodium acetate trihydrate to a pharmaceutically acceptable pH, such as a pH within a range of 5 to 8. Pharmaceutical compositons for injection (e.g. by intravenous, intraperitoneal, intradermal, subcutaneous, intramuscular or intraportal) or continuous infusion are suitably free of visible particulate matter and may comprise from 1 mg to 10 g of therapeutic antibody, typically 5 mg to 1 g, more specifically 5 mg to 25 mg or 50 mg of antibody. Methods for the preparation of such pharmaceutical compositions are well known to those skilled in the art. In one embodiment, pharmaceutical compositions comprise from 1 mg to 10 g of therapeutic antibodies of the invention in unit dosage form, optionally together with instructions for use. Pharmaceutical compositions of the invention may be lyophilised (freeze dried) for reconstitution prior to administration according to methods well known or apparent to those skilled in the art. Where embodiments of the invention comprise antibodies of the invention with an IgG1 isotype, a chelator of metal ions including copper, such as citrate (e.g. sodium citrate) or EDTA or histidine, may be added to the pharmaceutical composition to reduce the degree of metal-mediated degradation of antibodies of this isotype, see EP0612251. Pharmaceutical compositions may also comprise a solubiliser such as arginine base, a detergent/anti-aggregation agent such as polysorbate 80, and an inert gas such as nitrogen to replace vial headspace oxygen.

Effective doses and treatment regimes for administering the antibody of the invention are generally determined empirically and are dependent on factors such as the age, weight and health status of the patient and disease or disorder to be treated. Such factors are within the purview of the attending physican. Guidance in selecting appropriate doses may be found in e.g. Smith et al (1977) Antibodies in human diagnosis and therapy, Raven Press, New York but will in general be 1 mg to 10 g. In one embodiment, the dosing regime for treating a human patient is 1 mg to 1 g of therapeutic antibody of the invention administered subcutaneously once per week or every two weeks, or by intravenous infusion every 1 or 2 months. Such a dosage corresponds to 0.014-140 mg/kg, such as 0.014-14 mg/kg. Compositions of the present invention may also be used prophylatically.

4. Clinical Uses.

It will be appreciated that diseases characterised by elevated β-amyloid levels or β-amyloid deposits include Alzheimer's disease, mild cognitive impairment, Down's syndrome, hereditary cerebral haemorrhage with β-amyloidosis of the Dutch type, cerebral β-amyloid angiopathy and various types of degenerative dementias, such as those associated with Parkinson's disease, progressive supranuclear palsy, cortical basal degeneration and diffuse Lewis body type of Alzheimer's disease.

Most preferably, the disease characterised by elevated β-amyloid levels or β-amyloid deposits is Alzheimer's disease.

Although the present invention has been described principally in relation to the treatment of human diseases or disorders, the present invention may also have applications in the treatment of similar diseases or disorders in non-human mammals.

EXAMPLES

| Methods | |
|---|---|
| Biacore ™/Biacore 3000 | a device that allows measurement of real time kinetics of molecular interactions using SPR |
| SPR | (surface plasmon resonance) - physical phenomenon employed by Biacore ™ instruments for measurement of mass changes on sensor chip |
| CM5 | Biacore ™ sensor chip with general purpose surface coated with a carboxymethylated dextran matrix |
| ELISA | enzyme linked immunosorbent assay |
| SRU | SRU BIND ™ Biosensor technology allowing to monitor label-free biochemical interactions |
| Integra CL1000 | Mini-bioreactors sold by IBS Integra Biosciences |
| FMAT | fluorometric microvolume assay technology (Applied Biosystems) |
| ABi8200 | Applied Biosystems 8200 fluorescence macro confocal cellular detection system for FMAT |
| FPLC | Fast protein liquid chromatography |
| ProSepA HiTrap | Protein A columns for FPLC sold by GE Healthcare |

| Materials | |
|---|---|
| DMSO | dimethylsulphoxide |
| HEPES | N-(2-hydroxyethyl)piperazine-N'-(2-ethanesulfonic acid) |
| EDTA | ethylenediaminetetraacetic acid |
| Tris HCl | tris-(hydroxymethyl)aminomethane hydrochloride |
| NaCl | sodium chloride |
| Tween-20 | polyoxyethylenesorbitan monolaurate |
| BSA | bovine serum albumin |
| PBS | phosphate buffered saline |
| PFA | paraformaldehyde |
| IMS | industrial methylated spirit |
| DAB | 3,3'diaminobenzidine |
| DMEM | dulbecco's modified eagle's medium |
| FCS | fetal calf serum |
| Opti-MEM | modified eagle's medium based medium by Invitrogen/Gibco |
| Lipofectamine | cationic lipid based cell transfection agent sold by Invitrogen/Gibco |
| Transfast | liposomal transfection agent sold by Promega |
| Versene | metal ion chelating agent (ethylenediaminetetraacetic acid) |
| Glutamax | stable form of glutamine added to culture medium (dipeptide L-Ananyl-L-Glutamine supplement) |
| Histoclear | tissue clearing agent |
| HBS-EP buffer | General purpose Biacore ™ buffer containing 0.01M HEPES pH 7.4, 0.15M NaCl, 3 mM EDTA, 0.005% Surfactant P20 |

Generation of Mouse Monoclonal Antibody 2E7

Mouse monoclonal antibody 2E7 was generated from a conventional immunisation of mice. Mice were immunised with soluble or aggregated β-amyloid 1-40 and 1-42 formulated in Freund's adjuvant. Following final boost without adjuvant, splenocytes were fused with myeloma cells. Fused cells were grown in 96-well plates from which hybridoma supernatants were screened for potential leads. Selected antibody 2E7, which was obtained from the immunisation with soluble β-amyloid 1-40, was of murine IgG2a isotype and had beta-amyloid binding activity in the efflux assay described below and an affinity of 36.1 pM for beta-amyloid 1-40 when measured by Biacorem™, Method A(i) (Table 10A).

Epitope Mapping of 2E7

In order to finely map the binding of antibody 2E7 to the β-amyloid peptide, a peptide set (A) was utilised. Peptide set (A) consisted of a set of 31 12-mer overlapping peptides covering the complete sequence of the β-amyloid 1-42 peptide. Each sequential peptide was initiated at the sequential amino acid within the β-amyloid peptide, thus shifting the sequence covered between sequential peptides by a single amino acid. All peptides in set (A) contained a 3 amino acid C-terminal linker (glycine-serine-glycine) and a terminal biotinylated lysine residue. In addition, all peptides except peptide Aβ1 DAEFRHDSGYEVGSGK-biotin (SEQ ID No:15) were N-terminally acetylated. A second set of peptides (set (B)) consisted of sequential one amino acid C-terminal deletions from a peptide containing amino acids 1 to 10 of the p-amyloid sequence. All peptides in set (B) contained a 3 amino acid C-terminal linker (glycine-serine-glycine) and a terminal biotinylated lysine residue, but with additional glycine and serine residues to replace for deleted β-amyloid amino acids (Table 2). Thus all peptides in set (B) are of the same length.

TABLE 2

Sequences of biotinylated peptides (set (B)) that contained truncated N-terminal fragments of β-amyloid

| | |
|---|---|
| DAEFRHDSGYGSGGSK-biotin | (SEQ ID No: 7) |
| DAEFRHDSG--GSGSGSK-biotin | (SEQ ID No: 8) |

TABLE 2-continued

Sequences of biotinylated peptides (set (B)) that contained truncated N-terminal fragments of β-amyloid

| | |
|---|---|
| DAEFRHDS--GSGGSGGK-biotin | (SEQ ID No: 9) |
| DAEFRHD--GSGGSGGSK-biotin | (SEQ ID No: 10) |
| DAEFRH--GSGGSGGSGK-biotin | (SEQ ID No: 11) |
| DAEFR--GSGGSGGSGSK-biotin | (SEQ ID No: 12) |
| DAEF--GSGGSGGSGGSK-biotin | (SEQ ID No: 13) |
| DAE--GSGGSGGSGGGSK-biotin | (SEQ ID No: 14) |

Monitoring the Binding of 2E7 to β-amyloid Derived Peptides Using Optical Biosensors 96-well SRU Bind™ streptavidin-coated plates (SRU Biosystems) were washed with PBS containing 1% DMSO to remove glycerol and preservative. A volume of 50 ul/well was left to equilibrate to room temperature to provide a constant base line. Biotinylated peptides were diluted to approx. 0.3 ug/ml in PBS containing 1% DMSO and 50 ul of each added to wells and incubated for approximately 1 h. Replicate wells were prepared using different sectors of the plate and at least one no-peptide control well was used in each sector to reference subtract the data. After peptide capture the plate was washed with PBS containing 1% DMSO, leaving 50 ul of fresh buffer per well to provide a new base line on the reader. No decay of peptide from the surface was seen. The buffer was then replaced with 40 ul/well buffer containing test antibody at 20-64 nM. for 2 hours. It was found that antibody 2E7 only bound to the peptide encompassing amino acids 1-12 of the β-amyloid peptide in peptide set (A) (peptide Aβ1, SEQ ID No:15) This result implies that the aspartic acid at residue 1 is critical for binding to this peptide.

In order to further characterise the binding site of antibody 2E7, peptide set (B) was utilised. Using SRU BIND™ biosensor methodology antibody 2E7 showed negligible binding to the peptides encompassing amino acids 1-3 and 1-4 of the β-amyloid peptide (SEQ ID No:14 and 13). Binding to a peptide encompassing amino acids 1-7 of the β-amyloid peptide (SEQ ID No:10) was comparable to the peptide encompassing amino acids 1-12 of the β-amyloid peptide (from peptide set (A)). Binding to peptides encompassing amino acids 1-5 or 1-6 of the β-amyloid peptide (SEQ ID No:12 or 11) was observed, but weaker (as measured by stability after an additional washing step) than the binding to the peptide encompassing amino acids 1-7 of the β-amyloid peptide (SEQ ID No:10).

Thus it has been shown that only residues 1-7 of the β-amyloid peptide are required for full binding as measured using this methodology.

Surface Plasmon Resonance Assay

In addition to the experiments described above, the Biacore™ 3000 optical biosensor was used to monitor the binding of 2E7 antibody to selected β-amyloid sequence derived peptides. Binding was measured by injecting test antibodies at up to 64 nM for 5 minute over peptides captured on separate streptavidin chip surfaces (130-230 RU (resonance units)). A running buffer (HBS-EP) containing 0.01 M HEPES pH7.4, 0.15M NaCl, 3 mM EDTA and 0.005% Surfactant P20™ at 25° C. was used at a flow rate of 20 ul/min. All runs were double referenced against a blank streptavidin surface and blank injections. Analysis was carried out using the Biacore™ analysis software BlAevaluation™ version 4.1. Results from selected peptides in set (A) further confirmed the SRU BIND™ derived data indicating that 2E7 bound only to the peptide encompassing amino acids 1-12 (SEQ ID No:15) of the β-amyloid peptide with an apparent equilibrium constant KD of approximately 50 pM. Under the same conditions, 2E7 did not bind to the peptide encompassing amino acids 2-13 of the β-amyloid peptide.

Peptide Aβ2-13 AEFRHDSGYEVHGSGK-biotin (SEQ ID No:44)

The experimental method and conditions used allowed the detection of high but also lower affinity molecules—in the same experimental setup, by contrast to 2E7, another antibody recognising an N-terminal epitope of the β-amyloid peptide was shown to bind the 2-13 peptide (SEQ ID No:44) with an apparent KD of 7 nM. 2E7 did not bind to a selection of peptides in set (A) from mid regions of the β-amyloid peptide. In a separate experiment the β-amyloid 1-40 peptide was captured via its N-terminal aspartic acid residue that had been biotinylated. This peptide was captured onto a Biacore™ streptavidin coated chip as previously described. Antibody 2E7 injected at 66 nM for 1 minute could not bind this peptide. Therefore, it is concluded that the previously described N-terminal binding site was masked by the linker and capture method, thus further confirming the extreme N-terminus as containing the core binding site Binding to Cell Expressed Amyloid Precursor Protein (APP)

β-Amyloid is composed of peptides formed by proteolytic cleavage of a type I transmembrane precursor protein named amyloid precursor protein (APP). As APP has a large extracellular domain, binding to this protein could potentially initiate an antibody-dependent cellular cytotoxicity reaction (ADCC).

To characterise binding of antibody to cell-surface full length APP an FMAT™ ABI8200 based assay was utilised.

Transfection of HEK293T Cells with Wild Type APP DNA

HEK293T cells are maintained in DMEM F12 medium containing 10% (v/v) FCS and 1× Glutamax. Cells are seeded in 75 cm² tissue culture flasks and grown to 60-80% confluency (18-24 h) prior to transfection. For transfection, 9 ug of DNA, (either wild type APP DNA in PCDNA3.1 (Invitrogen) vector), or vector only controls, is mixed with 0.3 ml of Opti-MEM™ media. 30 ul Lipofectamine™ transfection agent is mixed with 0.3 ml Opti-MEM™ media and the two mixtures pooled. The pooled mixtures are incubated at room temperature for 30 min prior to the addition of a further 4.8 ml of Opti-MEM™ media. The final mixture is added to the cells (post washing with Opti-MEM™ media) for 5 h and 6 ml of 10% (v/v) newborn calf serum in DMEM is then added. 48 hrs post transfection, supernatant is removed and the monolayer washed in versene, and then 3 ml of Versene™ chelating agent is added to each flask, incubated for 5 mins at 37 C, and the detached cells pelleted at 200 g for 5 mins. The resultant cell pellet is gently resuspended in 1 ml of assay buffer (2% heat treated serum, 0.5% BSA, 0.1% NaN$_3$ in PBS pH7.4, filtered through a 0.2 um filter) to create a single cell suspension.

FMAT™ ABI8200 Based Assay

Test antibodies (2E7, LN27 (Zymed) mouse IgG to extracellular domain of APP as a positive control, and an antibody G210 which recognises the x-40 form of the β-amyloid peptide as a negative control) were diluted to 10 μg/ml in sterile filtered assay buffer (2% heat treat serum, 0.5% BSA, 0.1% NaN$_3$ in PBS pH7.2) in a polypropylene plate, and then a further six serial 1:1 dilutions were performed down the plate. Assay buffer only was used as a blank. 50 ul of a suspension of HEK293T cells transfected with wild type APP DNA (Experiment 1: 10,000 cells; Experiment 2: 20,000 cells) was added to each well of a 96 well plate, to which 5 ul of each of the antibody solutions were added to duplicate wells. 50 ul/well of F-MAT™ blue anti mouse IgG stock, (antibody is labelled using F-MAT™ blue monofunctional reactive dye kit from ABI, 4328408), diluted 1:500 (Experiment 1) and 1:1000 (Experiment 2) in assay buffer, was then added to each well and the plate briefly shaken and left to settle for 1 hr. The plate was then read using the ABI 8200 fluorescence macro confocal cellular detection system (Applied Biosystems).

Derived counts data were then interpreted using Excel™ spreadsheet software. Briefly, mock transfected counts were subtracted from the full length APP transfected cell counts to obtain a specific signal for each antibody. Two antibody concentrations that were on the linear part of the curve were chosen (1.25 and 0.63 ug/ml) and the background corrected derived counts at these concentrations expressed as the percentage of the LN27 antibody binding, and averaged over the two antibody concentrations. The resultant data is described in Table 3 (% of LN27 binding ±SE)

Thus, within this assay system, the binding of 2E7 to cell surface APP is indistinguishable from that of the negative control antibody G210.

TABLE 3

| antibody | Experiment 1 | Experiment 2 |
|---|---|---|
| LN27 | 100.0 ± 7.1 | 100.0 ± 4.7 |
| G210 | 5.5 ± 1.3 | 2.0 ± 1.6 |
| 2E7 | 9.9 ± 3.7 | 2.2 ± 1.4 |

Binding to Amyloid Precursor Protein Derived Peptide

The previously described epitope mapping studies have shown that antibody 2E7 binds to the extreme N-terminus of the β-amyloid peptide, with the aspartic acid residue at position 1 being essential for binding. This suggests that the antibody recognises a 'neo' epitope formed by cleavage of APP at the β-secretase site. This observation would suggest that antibody 2E7 should not recognise adjacent APP peptide sequence. To test this hypothesis an APP peptide (Peptide APP1, SEQ ID No:16) was synthesised which included residues 1-7 of the β-amyloid peptide and the five adjacent APP derived amino acids. Thus peptide APP1 contained contiguous amino acids from position 5 N-terminal to the BACE-1 cleavage site to position 7 C-terminal to the BACE-1 cleavage site and was N-terminally acetylated. The ability of antibody 2E7 to bind to the APP derived peptide APP1 and the β-amyloid 1-12 peptide (peptide Aβ1) was compared using Biacore™ methodology (as previously described for epitope mapping). Antibody 2E7 showed high affinity binding to the β-amyloid peptide Aβ-1, which contains the basic epitope 1-7. However, no binding was observed to the APP1 peptide which also contains the basic β-amyloid derived sequence 1-7.

```
Peptide Aβ1
DAEFRHDSGYEVGSGK-biotin         SEQ ID No: 15

APP1
AcNH-SEVKMDAEFRHDGSGK-biotin    SEQ ID No: 16
```

A combination of FMAT™ based cellular binding and Biacore™ based peptide mapping has been utilised to show that, in these formats, 2E7 has no binding affinity for the full length APP protein. Given that the aspartic acid residue at position 1 of the ™-amyloid peptide is required for binding, it is concluded that 2E7 only recognises the 'neo' N-terminus of ™-amyloid and hence should not bind cell surface expressed APP.

In Vivo Biological Activity $I^{125}$ β-Amyloid Efflux Model

A number of published studies have shown that β-amyloid antibodies can form complexes with β-amyloid peptide in the bloodstream. It is argued that this sequestration of peripheral β-amyloid allows for further efflux of CNS amyloid into the bloodstream (DeMattos RB, PNAS (2001), 98(15); 8850-8855). An acute pharmacodynamic model was developed to screen antibodies for their ability to complex with brain derived β-amyloid peptide in the bloodstream.

Anaesthesia (4% isoflurane) was induced in male C57/BL6J mice and maintained (1.5% isoflurane) in 100% oxygen. Animals were then placed in a stereotaxic frame. Following midline incision along the sagittal suture a bore hole was drilled through the skull and a guide cannula was inserted into the lateral cerebral ventricle (co-ordinates anterioposterior (AP) −0.5mm, lateral (L) +0.7mm, ventral (V) −2.5mm). A further two bore holes were drilled through the skull into which cortical screws were placed. The cannula was anchored in place by cyanoacrylate gel and the incision was sutured around the cyanoacrylate gel headcap. Post-operatively the mice received 0.3 ml saline subcutaneously and were placed in a warm environment to recover from anaesthesia. On recovery of the righting reflex, mice were housed singly and received 5 days standard post-op care. No procedures were permitted for a further 5 days or until pre-operative body weight was regained. Following recovery, cannula placement was verified by the angiotensin II drinking response. Each mouse received an intracerebroventricular (ICV) administration (5 μl) of 100 ng angiotensin II (AII) (made up in 0.9% saline). Following administration of AII, water intake was observed for 15 minutes. Mice with a positive dipsogenic response to AII (sustained drinking) were included in the studies, which commenced no sooner than five days post AII injection.

On the day of study the mice were placed for 5-10 minutes in a warm environment to induce vasodilation, necessary for ease of injection into the tail vein. Test antibody (600 μg) or PBS vehicle (dose volume no greater than 10 ml per kg body weight) was injected via the tail vein and mice were returned to their individual cages post-injection. At exactly one hour post tail vein injection, mice were slowly ICV injected (2 μl per minute) with 2 ng (1 μCi) of $I^{125}$ beta-amyloid 1-40 (Amersham Biosciences, UK) in a dose volume of 5 μl. At exactly four hours post ICV dose, 500 of trunk blood was collected and the radioactivity level measured on a scintillation counter.

Mice that had been injected into the tail-vein with 2E7 (n=6 per treatment group) showed a statistically significant increase in the radioactive signal (counts per minute—CPM) in 50 μl of trunk blood compared with the CPM signal detected in vehicle injected mice—(CPM—vehicle: 1339.7±496.2 vs. 2E7 4387.9±980.3; ANOVA:$F_{(2,13)}$=4.97, $p<0.05$. Post-hoc LSD: $p=0.01$ 2E7 vs. vehicle [post-hoc Duncans: $p=0.02$ 2E7 vs, vehicle]).

In two further studies with 2E7 conducted with the identical protocol, similar increases in amyloid efflux into blood when compared with vehicle injected controls were observed (CPM blood: Vehicle 352+/−113 versus 2E7 2397+/−353, and Vehicle 1281+/−312 versus 2E7 5291+/−885; ANOVA with post-hoc LSD test $p<0.001$ vs. vehicle).

Transgenic CNS β-Amyloid Lowering Models

1. β-Amyloid Load Following 4 Week Dosing of 2 Month Old TASTPM Mice

Male and female TASTPM transgenic mice (double-mutant APPswe×PS1.M146V, Howlett D R (2004) Brain Research 1017 (1-2) 130-136) aged between 61 and 65 days at the start of the study and were singly housed. Equal numbers of mice were assigned to each treatment group (N=12 per group) and were randomized according to gender and age. Treatment groups comprised the following: A: MOPC21 (antibody with unknown specificity, Holton et al (1987) J. Immunol 139(9) 3041-3049, negative control), B: 2E7 (test antibody). All antibodies were dissolved in PBS and were dosed by the intraperitoneal route. Irrespective of animal weight, 300 ug of antibody was administered. Animals were dosed twice weekly for four weeks. One day after the final dose, animals were euthanased by overdose with sodium pentobarbital. Brains were dissected and hemisected. Hemisected brain samples were collected into pre-weighed 2 ml eppendorf™ tubes and snap frozen. Samples were subsequently thawed, reweighed and 1 ml of 5M guanidine HCl containing Complete protease inhibitor™ tablets (Boehringer Mannheim) added, before the samples were homogenized and incubated at 4° C. for >90 min with constant agitation.

Samples were then diluted 1 in 10 into assay buffer (50 mM Tris HCl, pH7.4, 150 mM NaCl, 0.05% Tween-20+1% BSA), vortexed and spun at 20,000 G for 20 mins at 4° C. The supernatant was removed and added as triplicate samples to the assay plate.

The levels of Aβ40 and Aβ42 were measured using a sensitive plate based electrochemiluminescent immunoassay (BioVeris™) employing C-terminal specific β-amyloid antibodies (to Aβ40 or A(β2) labelled with Oritag™ specific label to facilitate detection (BioVeris™) used to capture either Aβ40 or Aβ42, along with a biotinylated N-terminal specific Aβ antibody. Antibody-Aβ complexes were captured with streptavidin coated beads that bind biotinylated antibodies (Dynabeads™, Dynal) incubated overnight at room temperature with vigorous mixing and assayed in a BioVeris™ M8 photodetector. Standard curves were constructed using human Aβ40 and Aβ42 peptides in assay buffer containing the required concentration of Guanidine HCl. Data was analysed using Excel Robosage™ statistical analysis software and Aβ levels expressed as pmole/g tissue.

In this paradigm, treatment with 2E7 antibody reduced CNS Aβ42 load by 37% ($p<0.001$). and CNS A1340 by 23% ($p<0.001$).

In subsequent studies under similar experimental conditions, 2E7 antibody reduced CNS Aβ42 load by 38% (Study 1, males only), 22% (Study 2, non-significant) and 39% (Study 3, males, p=0.001) and 13% (Study 3, females, non-significant) when compared to PBS treated animals. In these studies 2E7 also reduced CNS Aβ40 by 18% (Study 3, males, p=0.017) and offered a non-significant reduction in CNS Aβ40 by 25% (Study 1, males only), <1% (Study 2) and a non-significant increase of 3% (Study 3, females) when compared to PBS treated animals.

2. β-Amyloid Load Following 4 Month Dosing of 4 Month Old TASTPM Mice

Briefly, 4 month old TASTPM transgenic mice were dosed 300 μg of antibody once or twice weekly via an intraperitonial (i.p.) route. After 4 months of dosing CNS β-amyloid levels were measured by ELISA and plaque load was measured by immunohistochemistry. Between the ages of 4 and 8 months, the CNS β-amyloid load increases exponentially and consequently, plaque pathology rapidly develops (Howlett D R (2004) Brain Research 1017 (1-2) 130-136).

Mice were aged between 120 and 128 days at the start of the study and were singly housed. Similar numbers of mice were assigned to each treatment group (N=20 or 21 per group) and were randomized according to gender and age. Treatment groups comprised the following: A: PBS (vehicle) dosed twice weekly, B: 2E7 dosed once weekly, C: 2E7 dosed twice weekly, D: PBS dosed once weekly. A 300 microgram dose (79 microliters volume) of 2E7 was administered via the intraperitoneal route. Vehicle treated animals received the same volume of PBS. Animals were dosed for eighteen weeks. TASTPM mice are liable to suffer spontaneous seizures and as a result a number of animals died during the course of the study. Final numbers were as follows A: 4 females, 9 males; B: 5 females, 8 males; C: 4 females, 9 males; D: 2 females, 9 males. Two or four days after the final dose (equal numbers per group) animals were euthanased by overdose with sodium pentobarbital. A tail tip sample from each mouse was taken for confirmation of the genotype. Brains were dissected and hemisected. The right hemisphere was fixed by immersion in 4% paraformaldehyde and processed for histology. The left hemisphere was collected into pre-weighed 2 ml eppendorf™ tubes, frozen on dry ice and stored at −80° C. for subsequent analysis of amyloid content. Prior to analysis, samples were thawed, reweighed and 1 ml of 5M guanidine HCl containing Complete protease inhibitor™ tablets (Boehringer Mannheim) added, before the samples were homogenized and incubated at 4° C. for >90 min with constant agitation.

Samples were then diluted 1 in 10 into assay buffer (50 mM Tris HCl, pH 7.4, 150 mM NaCl, 0.05% Tween-20+1% BSA), vortexed and spun at 20,000G for 20 mins at 4° C. The supernatants were diluted a further 1:1000 and added as triplicate samples to the assay plate.

The levels of Aβ40 and Aβ42 were measured as for the 4 week dosing study.

An analysis of variance was used with treatment, sex and dosing schedule included in the model as fixed effects. All of the interactions between the three factors were also included. There were no significant differences between the two dosing schedules (once or twice weekly). With this experimental design, firstly it could be assessed if there were any significant differences between the dosing schedules and secondly, as there were no such significant differences, data from the two dosing schedules could be combined, thus increasing the power of the experiment by doubling the number of mice in the analysis.

In this paradigm, treatment with 2E7 antibody reduced CNS Aβ42 load by 22.5% (p=0.0152). Levels of CNS Aβ40 were also lowered by 12.1%, but this figure did not reach statistical significance (p=0.118).

A complex immunohistochemical analysis of these samples was performed to define the area of brain tissue showing plaque pathology. Sections were taken from the cortex at the level of the caudate and from the cortex at the level of the hippocampus. Adjacent sections were stained with either an Aβ40 or Aβ42 specific antibody or alternatively with the amyloid stain Congo Red. Using image analysis software, the area of the section stained for plaque was expressed as a percentage of the total section area.

After fixation, the PFA-immersed half brains were coronally cut in a brain matrix into 6×2 mm thick sections. These 2 mm sections will be referred to as sections A to F, A being the most rostral and F the most caudal. Sections A, B & C and D, E & F were placed in separate embedding cassettes numbered for each animal. Cassettes were held in PFA until ready for processing and embedding.

Embedding was undertaken on a Citadel™ 1000 (Shandon) tissue processor. All tissues received the following processing regimen:
70% IMS—1 hr
100% IMS—3×1 hr
100% ethanol—2 hr
100% isobutyl alcohol; 1×2 hr; 1×1.5 hr
Histoclear™—2×1.5 hr
Paraffin wax—2×2 hr On completion of the processing cycle, the wax impregnated tissue sections were transferred to molten-paraffin wax filled base moulds and embedded utilising a Histocentre™ (Shandon) paraffin embedding system. Tissue was embedded such that sections A, B & C went into one mould; D, E & F into a second mould. This was carried out for all sets of sections ie. each hemisected brain resulted in two wax blocks of three sections each. Sections were placed in the moulds such that the caudal surface of each piece became the future cutting surface. Care was taken to ensure that each section was pushed well down in the mould so that microtoming of each would occur in parallel. The perforated processing cassette was then carefully placed onto each mould which was then topped up with molten wax. Embedded blocks were then cooled on the refrigerated plate until they could be removed from the moulds. Blocks were stored at room temperature until required for microtoming. Blocks were cut at random and 5 micron sections floated onto prelabelled gelatine coated slides (Superfrost™, Erie Scientific Company) slides. Two sections were floated onto each slide. Wherever possible, consecutive sections were mounted and slides were numbered consecutively from 1 to 25. Fifty sections (25 slides) were taken from each block. Slides were dried on a hot plate and then stored at room temperature until required.

Immunohistochemistry was undertaken on sets of 30 slides. On each slide, the top section was labelled with an Aβ40 antibody (G30, rabbit polyclonal recognising x-40 β-amyloid), the lower section with the Aβ42 antibody, 20G10, monoclonal antibody recognising x-42 β-amyloid. A minimum of 5 sections per antibody per block were labelled.

Labelling was carried out as follows. Following dewaxing through Histoclear and graded alcohols, sections were immersed in 85% formic acid for 8 minutes and then blocked in 0.3% hydrogen peroxide for 30 minutes to block endogenous peroxidases. Antibodies G30 and 20G10 were both applied overnight at 1:1000 dilutions, sections being left at 4° C. Development of the sections was with the respective biotinylated anti rabbit and anti-mouse secondaries. Colour development was accomplished with a diaminobenzidine tetrahydrochloride staining kit (DAB™, Vector Labs). Sections were briefly counterstained with Mayer's hematoxylin before being dehydrated, cleared and cover-slipped.

Sections were left to dry for at least 48 hours before microscopy. Images were captured on a Leica DMRB™ microscope equipped with digital camera. Images were analysed using Qwin™ software (Leica) and results presented as % of the section area that was labelled by the A™ antibody.

An analysis of variance was used with treatment, sex and dosing schedule included in the model as fixed effects. All of the interactions between the three factors were also included. There were no significant differences between the two dosing schedules (once or twice weekly). With this experimental design, firstly we could assess if there were any significant differences between the dosing schedules and secondly, as there were no such significant differences, data from the two dosing schedules could be combined, thus increasing the power of the experiment by doubling the number of mice in the analysis.

In this paradigm, treatment with 2E7 antibody reduced plaque pathology as measured with an antibody recognising Aβ42. Plaque pathology was reduced by 27.1% (p=0.0026) in the cortex at the level of the hippocampus and 43% (p<0.0001) in the cortex at the level of the caudate. Plaque pathology was also reduced when measured with an antibody recognising Aβ40. Plaque pathology was reduced by 16.6% (p=0.0421) in the cortex at the level of the hippocampus and 17.3% (p=0.0342) in the cortex at the level of the caudate.

No evidence of microhaemorrhage (as determined by Perls' Prussian Blue) was observed in any mice from this study treated with vehicle or 2E7. This method visualises ferric iron (iron is an essential constituent of the oxygen-carrying haemoglobin found in red cells) by producing an insoluble blue compound. All levels of brain from all animals were clear.

Cognition Models

Following the 4 month dosing of 4 month old TASTPM mice as described above, these mice were tested in two models of cognition: the object recognition assay and the fear conditioning assay.

Object Recognition Assay

The object recognition assay exploits the animals' natural propensity to explore novel objects and relies on the animals' ability to recall an object which had been explored previously (familiar object). Eight month old TASTPM mice have been reported to demonstrate a deficit in the ability to distinguish between novel and familiar objects (Howlett et al., 2004) indicating impaired cognitive performance in these animals. In this study, however, 8 month-old TASTPM mice treated with vehicle failed to demonstrate cognitive impairment i.e. they were able to distinguish between novel and familiar objects. There was therefore no window to investigate any potential therapeutic effect resulting from treatment with 2E7.

Fear Conditioning Assay

The fear conditioning model was designed to test the animals' ability to correlate a previous painful stimulus with a contextual or cued signal and recall this when presented with the same context or tone following Xh delay. In this study 8-month old TASTPM mice treated with vehicle (once or twice weekly) exhibited a deficit in contextual differentiation indicative of cognitive impairment in these animals. This deficit was unaffected by treatment with 2E7 when administered once of twice weekly 4 Month Dosing of 6 Month Old TASTPM Mice This study involved the administration of 2E7 (300 ug i.p. twice weekly) to TASTPM mice for 4 months, starting at 3 months of age. Control animals received IgG2A in PBS. As described above, brains were dissected and hemisected. The right hemisphere was fixed by immersion in 4% paraformaldehyde and processed for histology. The left hemisphere was collected into pre-weighed 2 ml eppendorf™ tubes, frozen on dry ice and stored at −80° C. for subsequent analysis of amyloid content.

A preliminary analysis of a single section from each of a random selection of brain samples (n=6 vehicle, n=7 2E7 treated group) by IHC was undertaken using the same general protocol as above. Statistical analysis (Student's t-test) shows that there was a significant decrease in Aβ42 plaque load in thalamus (71.9%, p=0.007) and in thalamus+cortex+hippocampus (54.1%, p=0.022) in mice dosed with 2E7 but no significant change in Aβ40.

For biochemical measurement of brain Aβ40 and Aβ42, samples were processed and measured as above (dilution factor 1:10,000). Aβ42 was significantly decreased (p=0.01) by 29.9% in mice dosed with 2E7 (n=12 control, n=16 treated). Aβ40 concentrations were also decreased (22.6%) but this decrease failed to reach statistical significance (p=0.052).

Cloning of Hybridoma Variable Regions

Variable Region Sequences

Total RNA was extracted from 2E7 hybridoma cells and heavy and light variable domain cDNA sequences were then generated by reverse transcription and polymerase chain reaction (RT-PCR). The forward primer for RT-PCR was a mixture of degenerate primers specific for murine immunoglobulin gene leader-sequences and the reverse primer was specific for the antibody constant regions, in this case murine isotype IgG2a for the heavy chain and murine kappa for the light chain. Primers were designed according to the strategy described by Jones and Bendig (Bio/Technology 9:88, 1991). RT-PCR was carried out in duplicate for both V-region sequences to enable subsequent verification of the correct V-region sequences. The V-region products generated by RT-PCR were cloned (Invitrogen TA Cloning Kit) and sequence data obtained.

2E7 $V_H$ Amino Acid Sequence
(SEQ ID No: 17)
```
EVKLVESGGGLVQPGGSLKLSCAVSGFTFSDNGMAWVRQAPRKGPEWI
AFISNLAYSIDYADTVTGRFTISRDNAKNTLYLEMSSLRSEDTAMYYC
VSGTWFAYWGQGTLVTVSA
```

2E7 $V_H$ DNA Sequence
(SEQ ID No: 18)
```
GAGGTGAAGCTGGTGGAGTCTGGGGGAGGCTTAGTGCAGCCTGGAGGG
TCCCTGAAACTCTCCTGTGCAGTCTCTGGATTCACTTTCAGTGACAAC
GGAATGGCGTGGGTTCGACAGGCTCCAAGGAAGGGGCCTGAGTGGATA
GCGTTCATTAGTAATTTGGCATATAGTATCGACTACGCAGACACTGTG
ACGGGCCGATTCACCATCTCTAGAGATAATGCCAAGAATACCCTGTAC
CTGGAAATGAGCAGTCTGAGGTCTGAGGACACGGCCATGTACTATTGT
GTAAGCGGGACCTGGTTTGCTTACTGGGGCCAAGGGACTCTGGTCACT
GTCTCTGCA
```

2E7 $V_L$ Amino Acid Sequence
(SEQ ID No: 19)
```
DVVLTQTPLSLPVSLGDQASISCRVSQSLLHSNGYTYLHWYLQKPGQS
PKLLIYKVSNRFSGVPDRFSGSGSGTDFTLKISRVEAEDLGVYFCSQT
RHVPYTFGGGTKLEIK
```

2E7 $V_L$ DNA Sequence
((SEQ ID No: 20)
```
GATGTTGTGCTGACCCAAACTCCACTCTCCCTGCCTGTCAGTCTTGGA
GATCAAGCCTCCATCTCTTGCAGAGTTAGTCAGAGCCTTTTACACAGT
AATGGATACACCTATTTACATTGGTACCTGCAGAAGCCAGGCCAGTCT
```

```
                                    -continued
CCAAAGCTCCTGATCTACAAAGTTTCCAACCGATTTTCTGGGGTCCCA
GACAGGTTCAGTGGCAGTGGATCAGGGACAGATTTCACACTCAAGATC
AGCAGAGTGGAGGCTGAGGATCTGGGAGTTTATTTCTGCTCTCAAACT
AGACATGTTCCGTACACGTTCGGAGGGGGGACCAAGCTGGAAATAAAA
```

Complementarity Determining Regions (CDRs) are underlined in the amino acid sequences.

Cloning and Expression of 2E7 Chimera

A chimeric 2E7 antibody (2E7c) consisting of the parent murine V regions grafted on to human IgG1 (Fc mutated (L235A, G237A)) for the heavy chain or human C kappa regions for the light chain was generated in order to express recombinant antibody material that could be used to confirm the correct cloning of functional murine V regions. DNA encoding 2E7 murine heavy and light chain V regions and endogenous murine signal sequences was cloned in frame into the mammalian expression vectors RLD-bshe (for the heavy chain) and RLN-bshe (for the light chain) already containing human constant regions (IgG1 Fc mutated (L235A, G237A) or human C kappa, respectively).

Elements of RLD-bshe expression vector for heavy chain expression:

| Base Pairs | Description of DNA segment |
|---|---|
| 0-1014 | Promoter (SV40/RSV) |
| 1015-2442 | Antibody heavy chain |
| 2443-2765 | Poly A |
| 2766-3142 | BG Promoter |
| 3239-3802 | DHFR |
| 3803-4162 | Poly A |
| 4163-6322 | Total backbone |
| 5077-5937 (complementary strand) | Beta lactamase |

(position of elements and overall size of vector given above are for illustration purposes only and will depend upon the size of the antibody chain insert)

Elements of RLN-bshe expression vector for light chain expression:

| Base Pairs | Description of DNA segment |
|---|---|
| 0-1014 | Promoter (SV40/RSV) |
| 1015-1731 | Antibody light chain |
| 1732-2051 | Poly A |
| 2388-2764 | BG Promoter |
| 2774-3568 | Neomycin |
| 3569-3876 | Poly A |
| 3877-6063 | Total backbone |
| 5077-5937 (complementary strand) | Beta lactamase |

(position of elements and overall size of vector given above are for illustration purposes only and will depend upon the size of the antibody chain insert)

Clones with correctly cloned $V_H$ and $V_L$ sequences were identified and plasmids prepared for expression in suspension culture CHO cells. Expressed 2E7c antibody was purified from cell culture supernatant by protein A chromatography on a FPLC system, and then tested for binding to Aβ by ELISA and SPR using Biacore™ technology. The results indicated that the correct 2E7 mouse V regions were cloned and expressed, resulting in a functional antibody with similar characteristics to the parent murine antibody 2E7.

Light Chain Humanisation

A human acceptor sequence with the Genpept ID CAA51135 (SEQ ID No:24) and Genbank Accesion No X72467, which had 77% identity on the amino acid level (including CDRs) was selected as the acceptor framework. Construct L1 is a graft of the murine CDRs from the 2E7 VL domain into this acceptor framework.

Heavy Chain Humanisation

Human sequence Genbank accession No M99675 (SEQ ID No:21) an allele of the VH3-48 gene with 74% identity on the amino acid level (including CDRs 1 and 2) to the 2E7 mouse variable heavy region was selected as the human heavy chain acceptor framework together with the human JH4 minigene. Three humanised variable heavy chain variants were designed based on the M99675 sequence and JH4. H1 is a graft of the murine CDRs using the Kabat definition with two additional framework back mutations at positions 93 and 94. H2 and H3 were both derived from H1, but incorporated one additional framework mutation which were different in each construct; (positions 24 and 48 respectively; see Table 4).

TABLE 4

| Construct | Template frameworks | Residue (Kabat#) | Human | Mouse |
|---|---|---|---|---|
| H1 | M99675 and JH4 | 93, 94 | A and R respectively | V and S respectively |
| H2 | H1 | 24 | A | V |
| H3 | H1 | 48 | V | I |

Construction of Humanised Heavy and Light Chain DNA

Humanised V regions were synthesised de novo by build up of overlapping oligos and PCR amplification. Restriction sites for cloning into mammalian expression vectors RLD-bshe and RLN-bshe and human immunoglobulin signal sequences derived from the chosen human acceptor frameworks were included. The DNAs encoding the humanised V regions (H1 (SEQ ID NO:27), H2 (SEQ ID NO:29), H3 (SEQ ID NO:31), L1 (SEQ ID NO:33)) together with signal sequences and restriction sites were then cloned in frame into mammalian expression vectors: H1, H2 and H3 into RLD-bshe to generate DNA encoding three full length human IgG1 Fc mutated heavy chains each containing mutations L235A and G237A, full length H1 (SEQ ID NO:35), full length H2 (SEQ ID NO:37) and full length H3 (SEQ ID NO:39); L1 was cloned in frame into RLN-bshe containing the DNA encoding human kappa constant region to generate DNA encoding a full length human kappa light chain (SEQ ID NO:41).

Representative Examples of Expression of Humanised Heavy and Light Chain Antibody Combinations CHOK1 cells were transiently transfected at small scale with all combinations of humanised light and heavy chain DNA constructs: L1+H1, L1+H2, L1+H3 (SEQ ID Nos: 35+41, 37+41, 39+41) in 6-well plates. CHOK1 cells passaged in DMEM F12, with 5% ultra low IgG foetal bovine serum and 2 mM glutamine were grown to confluency in 6-well plates. The confluent cells were transfected with a total of 7.5 μg DNA: 30 μg Transfast lipid (Promega) in Optimem Glutamax medium (Invitrogen). Transfected cells were incubated at 37° C. with 5% $CO_2$. At 72 hours supernatants were harvested and assayed for antibody concentration and then tested for binding to human Aβ by ELISA. Humanized L1 combined with the three humanized heavy chains all expressed complete antibody that bound to human Aβ.

Humanized antibodies were also expressed in large scale transient CHOK1 cell transfections using liposomal delivery of DNA (eg TransFast (Promega)) and expression in culture bottles. For optimization of expression levels in transient transfections a heavy to light chain expression vector DNA ratio of 1:6 was used. Material from transient transfection was purified using ProSepA columns or FPLC with ProSepA HiTrap columns.

Assessment of 2E7 Humanised Variants H1L1, H2L1 and H3 L1 in β-Amyloid Binding ELISA 2E7 H1L1, H2L1 and H3L1 humanised variants were assessed for binding to human Aβ peptide (1-40) biotinylated at the C terminus. The chimeric 2E7 was used as a reference. Tables 5-7 show results with various batches of purified material from large scale transient transfections.

TABLE 5

| ELISA | MAb | $EC_{50}$ (μg/ml) | Standard Error |
|---|---|---|---|
| Aβ binding | 2E7c Chimera | 0.033 | 0.00144 |
| | H1L1 | 0.035 | 0.00142 |
| | H2L1 | 0.048 | 0.00202 |
| | H3L1 | 0.044 | 0.00105 |

TABLE 6

| ELISA | MAb | $EC_{50}$ (μg/ml) | Standard Error |
|---|---|---|---|
| Aβ binding | 2E7c Chimera | 0.043 | 0.00183 |
| | H1L1 | 0.051 | 0.00164 |
| | H2L1 | 0.044 | 0.00191 |
| | H3L1 | 0.055 | 0.00094 |

TABLE 7

| ELISA | MAb | $EC_{50}$ (μg/ml) | Standard Error |
|---|---|---|---|
| Aβ binding | 2E7c Chimera | 0.044 | 0.00169 |
| | H1L1 | 0.047 | 0.00265 |
| | H2L1 | 0.041 | 0.00174 |
| | H3L1 | 0.040 | 0.00116 |

These results indicated very similar Aβ binding profiles for each of the 2E7-derived humanised variants. Comparison of the EC50 values to the 2E7c showed little loss of Aβ binding activity had been incurred through the humanization process.

Comparison of 2E7 Humanised Variants by Competition ELISA

2E7c chimeric and humanised antibodies H1L1, H2L1 and H3L1 were assessed for their ability to inhibit the binding between the human Aβ peptide and the parental mouse 2E7 MAb in a competition ELISA.

Two types of competition ELISA were established in order to compare the Aβ binding activity of the three humanised variants compared to the 2E7 chimeric antibody.

1) Immobilised β-amyloid; biotinylated human Aβ peptide (1-40) was immobilized through Streptavidin on ELISA plates Mouse 2E7 antibody was added at a constant concentration along with a dilution series of 2E7-derived humanised variant antibodies. Bound mouse 2E7 MAb was then detected with anti-mouse IgG conjugate. Table 8 shows results of two assays.

TABLE 8

| Competitor MAb | Experiment 1 $IC_{50}$ (μg/ml) | Standard Error | Experiment 2 $IC_{50}$ (μg/ml) | Standard Error |
|---|---|---|---|---|
| 2E7c Chimera | 1.31 | 0.20 | 1.29 | 0.13 |
| H1L1 | 1.62 | 0.40 | 1.76 | 0.21 |

TABLE 8-continued

| Competitor MAb | Experiment 1 $IC_{50}$ (μg/ml) | Standard Error | Experiment 2 $IC_{50}$ (μg/ml) | Standard Error |
|---|---|---|---|---|
| H2L1 | 1.28 | 0.26 | 1.66 | 0.28 |
| H3L1 | 1.53 | 0.16 | 1.39 | 0.23 |

2) β-amyloid in solution; a constant concentration of β-amyloid was pre-incubated with a dilution series of humanised 2E7 antibody variants—the mixture including complexed and free amyloid was added for a short time to wells containing immobilised mouse 2E7 MAb. The amount of free β-amyloid that was still available for binding the immobilised parental 2E7 MAb was then detected. Table 9 shows results of two assays.

TABLE 9

| Competitor MAb | Experiment 1 $IC_{50}$ (μg/ml) | Standard Error | Experiment 2 $IC_{50}$ (μg/ml) | Standard Error |
|---|---|---|---|---|
| 2E7c Chimera | 0.052 | 0.006 | — | — |
| H1L1 | 0.114 | 0.014 | 0.140 | 0.024 |
| H2L1 | 0.075 | 0.009 | 0.119 | 0.014 |
| H3L1 | 0.069 | 0.004 | 0.115 | 0.013 |

All humanised antibody variants inhibited the binding of mouse 2E7 MAb to β-amyloid with a very similar profile. $IC_{50}$ values generated for H2L1 and H3L1 variants were consistently close to that of the 2E7c chimera (where used), which had the highest inhibitory activity in both assays. However, variant H1L1 showed a somewhat reduced inhibitory activity in both assays, indicating a possible slightly lower affinity for β-amyloid.

SPR Biacore™ Analysis of 2E7, 2E7c, H1L1, H2L1, H3L1

The kinetics parameters of recombinant mouse 2E7 MAb, chimeric 2E7c and humanized variants H1L1, H2L1 and H3L1 binding to human beta-amyloid peptide (1-40) and (1-42) were assessed using Biacore™ analysis on a Biacore™ 3000. Two different assay formats were used.

Method A (i) Briefly, <20 resonance units of beta-amyloid 1-40 peptide (biotinylated at the C-terminus) were captured on a streptavidin biosensor chip (as used for Table 10A). The antibodies were diluted down in HBS-EP buffer and passed over the streptavidin/beta-amyloid surface at concentrations ranging from 0.001 nM-8 nM (for Table 10A). Two separate runs were carried out; each run was carried out on a new streptavidin/beta-amyloid surface. Runs 1 and 2 were essentially the same though there were some differences in the parameters used; Run 1 was carried out using a chip surface on which 16 RU's of beta-amyloid were captured, and antibody concentrations of 0.001 nM-8 nM were used, an association time of 4 minutes and a dissociation time of 20 minutes were used at a flow rate of 50 μl per minute. For Run 2, less than 10 RU's of beta-amyloid were captured and antibody concentrations of 0.003125 nM-8 nM were used. The flow rate and association times were the same as Run 1, however the dissociation time was reduced to 15 minutes.

(ii) Beta amyloid (1-40) and (1-42) were amine-coupled on different surfaces of a CM5 biosensor chip to a level of <20 resonance units (as used for Table 10B). The antibodies were diluted down in HBS-EP buffer and passed over the biosensor/beta-amyloid surface at concentrations ranging from 1 nM-64 nM (as used for Table 10B).

Method B

In the second instance the assay was reversed, in that antibodies were first captured to a level of 1000-2500 resonance units on an anti-mouse IgG polyclonal antibody surface (for recombinant mouse 2E7 MAb) or a protein A surface (for humanized H2L1) of a CM5 biosensor chip. Freshly prepared beta-amyloid (1-40) or (1-42) was diluted down in HBS-EP buffer and passed over the captured-antibody surface at concentrations ranging from 4-500 nM (Table 10C and 10D).

In both methods, regeneration was via a pulse of 100 mM $H_3PO_4$, and for Table 10A data also followed by a pulse of 50 mM NaOH. The surface was shown to be stable and unaffected by regeneration. All runs were double referenced against buffer blank injections. Analysis was carried out using the Biacorem™ analysis software BIAevaluation version 4.1.

Results

Method A(i) was used to rank order the antibodies by beta-amyloid binding kinetic data. The data obtained is shown in Table 10A. This shows that the parental 2E7 Mab has a KD of 36.1 pM for streptavidin-captured beta-amyloid. The chimeric mouse-human antibody showed a slightly reduced KD of 45.8 pM and the humanised constructs range from 54 (H2L1) to 93.6 pM (H1 L1). In conclusion this demonstrates that the humanisation procedure had been very successful and very little affinity had been lost. The additional backmutations introduced for H2 and H3 had a small but beneficial effect, although the differences between H2 and H3 constructs are within the standard deviations for these experiments.

TABLE 10A

| Antibody | | ka | kd | KD(pm) |
|---|---|---|---|---|
| 2E7 | Run 1 | 1.61e6 | 6.17e−5 | 38.3 |
| | Run 2 | 1.69e6 | 5.72e−5 | 33.8 |
| | Average(SD) | 1.65e6 | 5.97e−5 | 36.1(3.2) |
| c2E7 | Run 1 | 1.34e6 | 6.44e−5 | 48.1 |
| | Run 2 | 1.3e6 | 5.65e−5 | 43.5 |
| | Average(SD) | 1.32e6 | 6.10e−5 | 45.8(3.3) |
| H1L1 | Run 1 | 5.60e5 | 5.32e−5 | 95.0 |
| | Run 2 | 6.37e5 | 5.87e−5 | 92.2 |
| | Average(SD) | 5.99e5 | 5.60e−5 | 93.6(2.0) |
| H2L1 | Run 1 | 9.91e5 | 5.76e−5 | 58.1 |
| | Run 2 | 1.1e6 | 5.49e−5 | 49.8 |
| | Average(SD) | 1.05e6 | 5.63e−5 | 54.0(5.9) |
| H3L1 | Run 1 | 8.24e5 | 6.26e−5 | 76.0 |
| | Run 2 | 8.3e5 | 4.75e−5 | 57.2 |
| | Average(SD) | 8.27e5 | 5.47e−5 | 66.6(13.3) |

Method A(ii) was used to confirm that the additional two amino-acid residues on the C-terminus of beta-amyloid (1-42) compared to beta-amyloid (1-40) did not significantly alter the binding properties of 2E7 and H2L1. The data obtained is shown in Table 10B and did confirm this.

TABLE 10B

| Antibody | Beta-amyloid | ka ($Ms^{-1}$) | kd ($s^{-1}$) | KD (pM) |
|---|---|---|---|---|
| 2E7 | 1-40 | 4.05e5 | 1.28e−4 | 317 |
| | 1-42 | 3.82e5 | 1.51e−4 | 394 |
| H2L1 | 1-40 | 3.33e5 | 1.22e−4 | 366 |
| | 1-42 | 3.40e5 | 1.55e−4 | 456 |

Method B was used to negate avidity effects potentially seen in the first assay format.

Avidity effects, caused by both Fab domains of a single antibody molecule binding at the same time to two adjacent beta-amyloid molecules on the biosensor surface (or in multimeric forms of beta-amyloid), would increase the apparent affinity of binding. Affinity measurements obtained using Method B are shown in Table 10C.

TABLE 10C

| Antibody | ka ($Ms^{-1}$) | kd ($s^{-1}$) | KD (nM) With Standard Deviation n = 3 |
|---|---|---|---|
| 2E7 | 2.83e5 ± 0.54e5 | 4.28e−4 ± 0.65e−4 | 1.58 ± 0.55 |
| H2L1 | 1.06e5 ± 0.27e5 | 7.50e−4 ± 0.50 | 7.32 ± 1.64 |

Evidence that this assay provided true 1:1 binding affinities was obtained when Fab fragments of H2L1, obtained by papain digestion, bound streptavidin-captured beta-amyloid (1-40) by a similar method to Method A(i) with an estimated KD of 2.4 nM.

Method B was also used to confirm that the additional two amino-acid residues on the C-terminus of beta-amyloid (1-42) compared to beta-amyloid (1-40) did not significantly alter the binding properties of an identical sequence clone to mouse 2E7 MAb, named 2F11. The data obtained is shown in Table 10D.

TABLE 10D

| Antibody | Beta-amyloid | ka ($Ms^{-1}$) | kd ($s^{-1}$) | KD (nM) |
|---|---|---|---|---|
| 2F11 | 1-42 | 2.39e5 | 2.74e−4 | 1.14 |
| 2F11 | 1-40 | 2.99e5 | 3.92e−4 | 1.31 |

In a study similar to the epitope mapping study on 2E7 using the Surface Plasmon Resonance assay described above, H2L1 behaved similarly to 2E7 in binding to the peptide encompassing amino acids 1-12 (Aβ1, SEQ ID No:15) of the β-amyloid peptide and not to the peptide encompassing amino acids 2-13 of the β-amyloid peptide (Aβ2-13, SEQ ID No:44).

Activity of H2L1 in the $I^{125}$ β-Amyloid Efflux Model

In order to functionally compare the humanised H2L1 with the parent mouse monoclonal 2E7, both were tested on the same day in the $I^{125}$ β-amyloid efflux model described above.

Both H2L1 and 2E7 significantly increased counts per minute (CPM) in blood compared with vehicle control. CPM of radioactivity in blood was as follows (Vehicle: 1940±166; 2E7: 10065±1386; H2L1: 10913±1535). Statistics used were ANOVA with post-hoc LSD test. n=7 vehicle, n=6 2E7, n=6 H2L1, ($p<0.001$ for each test compound vs. vehicle).

This data provides further evidence that the humanised H2L1 antibody has retained the functional properties shown with the mouse 2E7 molecule.

Investigation of the Pharmacokinetics of H2L1 and 2E7

The terminal half life of test antibody in mice was investigated. Test antibody was administered by a 1 h intravenous infusion to 4 mice to achieve a target dose of 400 ug per mouse. Serial blood samples were taken from each mouse up to 5 days after dosing (one mouse from the 2E7 group did not complete the study and one from the H2L1 group was removed from subsequent analysis because it became apparent the dose had not been administered i.v.). Antibody levels were measured using a β-amyloid capture ELISA.

Analysis of the data indicates that the humanised antibody H2L1 has a terminal half life of circa 82 hours in mice (Table 11), which is comparable to that of the parent mouse monoclonal antibody 2E7 (circa 75 hours).

TABLE 11

| Parameter | Mean ± SD (n = 3) |
|---|---|
| Cmax (ug/mL) | 291 ± 43 |
| Tmax (h) # | 2.0 (1.1-2.1) |
| CLp (mL/h/kg) | 0.9 ± 0.1 |
| t½ (h) | 82 ± 4 |
| Vss (mL/kg) | 94 ± 12 | median and range
Cmax Observed maximum plasma concentration.
Tmax Time of the observed maximum plasma concentration
CLp Total plasma clearance; Dose/AUC$_{(0-inf)}$.
t½ Terminal phase half-life was determined as the ratio of ln2/z where z is the terminal phase rate constant; calculated using unweighted linear regression analysis (after log transformation) on those concentration-time pairs occurring after the visually assessed onset of the terminal log-linear phase.
Vss Volume of distribution at steady-state; CLp × MRT$_{0-inf}$.

Effect of H2L1 on Peripheral Amyloid Load in Aged Non-Human Primates A study was conducted in aged Cynomolgus monkeys (approximately 15 years old) to investigate the exposure response relationship with respect to amyloid/H2L1 complex formation and clearance and the subsequent effects on CSF and CNS amyloid levels. Weekly lumbar CSF (taken under ketamine sedation) and blood samples were collected 3 weeks prior to 1$^{st}$ dose of H2L1. Immediately following sampling on week 3, animals received placebo (n=10), 0.1 mg/kg (n=5), 1 mg/kg (n=5) or 10 mg/kg (n=10) H2L1 and then every 2 weeks for 12 weeks. Blood samples for plasma analysis of H2L1 and total A$\beta_{42}$ were taken weekly. CSF samples for quantification of A$\beta_{40/42}$ were collected every 2 weeks. Following completion of the dosing period, animals were euthanased for the purpose of brain quantification of beta-amyloid by biochemical analyses as described above and investigation of microhaemorrhage. In the lowest dose group (0.1 mg/kg), animals were euthanased in a staggered fashion to evaluate the potential time course effect in brain levels as a consequence of termination of dosing and hence saturation of the plasma amyloid pool.

This study was approved by the Institutional Animal Care and Use Committee (IACUC) of MACCINE Pte Ltd, or "Maccine" prior to start of the experimental phase. The IACUC protocol number was #08-2006. GSK has performed a site visit of Maccine and has reviewed their ethical review process and found it acceptable Plasma samples were serially diluted 1:10 to 1:50000 and added to A$\beta_{40}$ coated ELISA plates. Standard curves were created ranging from 0-10 µg/ml H2L1 in diluent. Following an overnight incubation at 4° C. H2L1 was visualised using anti-human IgG horseradish peroxidase (Amersham—diluted 1:2000 in diluent) and tetramethylbenzidene detection system. Following single and repeat iv bolus administration, plasma levels of H2L1 appeared to increase in a dose dependent fashion. There was no evidence of severe non-linearities in the pharmacokinetics, indicating that for the majority of the dosing interval, excess molar concentrations of H2L1 in the plasma compared with free amyloid levels were achieved.

Total A$\beta_{42}$ was measured in neat plasma using a commercially available A$\beta$ 1-42 ELISA kit (Innogenetics) in accordance with the manufacturers instructions, with standard curves ranging from 500-7 pg/ml created in kit diluent. Samples and standards are incubated overnight at 4° C. before assaying in duplicate according to kit instructions. It should be noted that due to the interference of the detection antibody supplied with the A$\beta_{42}$ assay, this kit cannot be used to measure free A$\beta_{42}$ levels but measures the apparent 'total' A$\beta_{42}$. There was a dose and concentration dependent increase in A6$_{42}$ (with plateau levels of approximately 300, 125 and 25 pg/ml detected following 10, 1 or 0.1 mg/kg H2L1 respectively).

From the analysis, the increase in the "total A$\beta_{42}$" is likely to be due to the result of a significant efflux of amyloid from outside the plasma pool, that appeared dependent upon H2L1 concentrations >1 ug/mL, and did not appear to be a result of lack of clearance of complex. This was evident by the elimination rate of the total A$\beta_{42}$ as well as the fluctuation in the total levels over a dosing interval.

To date only the plasma analysis has been completed and fully analysed. However preliminary analysis indicates that there was a trend towards reduction in CSF and increase in the hippocampal level of 'total' A$\beta$42 (measured as generally described above) following treatment with 10 mg/kg H2L1.

In some brain sections, small areas of microhaemorrhage were detected as shown by the Perls' Prussian Blue staining method. This method visualises ferric iron (iron is an essential constituent of the oxygen-carrying haemoglobin found in red cells) by producing an insoluble blue compound. However there was no difference in the incidence between vehicle and drug treated animals.

Analyses on Aged Cynomoloqus Macaque Monkeys for Beta Amyloid Plaques in the Brain and Total Beta Amyloid in the Plasma Cerebral spinal fluid (CSF) and tissue parameters of human AD have been displayed in the cynomolgus monkey. The aged cynomolgus monkey has been shown to have evidence of amyloid deposition. (Covance, The cynomolgus monkey as a model for Alzheimer's disease. In: Buse E, Habermann G, Friderichs-Gromoll S, Kaspereit J, Nowak P and Niggemann K, editors. Poster Presentation at the 44th Annual Meeting of the Society of Toxicology, New Orleans, Louisiana, 6 to 10 Mar. 2005). The potential for H2L1 to elicit an inappropriate response (such as encephalitis) in an aged brain was investigated in old, ca. 20 years, ex-breeding female monkeys. In addition, safety, treatment-related microhaemorrhage, neutralization/clearance of test material, hypersensitivity, and immune complex disease were also investigated following intravenous administration for 8 weeks in two-weekly intervals. In addition CNS and blood samples were analysed for levels of A$\beta_{40/42}$.

Study Design

Groups of 5 (group 1), 9 (group 2) or 10 (group 3) geriatric female cynomolgus monkeys were given 0 (vehicle), 50 or 100 mg/kg/dosing day H2L1 in vehicle (4 ml/kg) every second week for 8 weeks intravenously by slow bolus administration. The vehicle consisted of sodium acetate trihydrate 6.81 mg/mL, disodium edetate dehydrate 0.0186 mg/mL, polysorbate 80 0.2 mg/mL, and L-Arginine base 10 mg/mL, the pH was 5.5. Dose levels were chosen to investigate dose levels that were 5 and 10 fold intended clinical dose levels.

The following evaluations were performed pre-dose, daily (clinical signs, body weight, food consumption), week 4 and the week before necropsy: in-life animal observations, body weight, body temperature, haematology, clinical chemistry (including cerebrospinal fluid [CSF] analysis), urinalysis, and cytokine determination in CSF. Following necropsy, organ weights, macroscopic observations, and microscopic observations of the brain, cervical spinal cord and gross lesions were conducted on all animals. Toxicokinetic evaluation was performed after each dosing.

Results

There were no unscheduled deaths, and there were no signs which indicated an influence of the test item on the general condition of the animals at the administered doses. The only remarkable observations in clinical pathology (hematology and serum chemistry) were concluded to be age- and not test article related.

Systemic exposure to H2L1 (as measured by $AUC_{0-1}$, and $C_{max}$) increased approximately in proportion to dose. For both dose groups, there was no marked change ($\geq$2-fold) in systemic exposure between the 1st dose and 4th dose sampling periods.

There were no signs of inflammatory reactions in the brain detected by CSF-analysis, and there were no macroscopic or microscopic findings at necropsy that suggested a test item influence, specifically no microhaemorrhage or encephalitis.

This study was conducted in compliance with the Good Laboratory Practice Regulations as outlined in German Chemical Law, annex 1 and 2 to §19a Chemikalien Gesetz, June 2002, the OECD Principles of Good Laboratory Practice (revised 1997, issued January 1998) ENV/MC/CHEM (98) 17, the Consensus Document "The Application of the OECD Principles of GLP to the Organisation and Management of Multi-Site Studies" ENV/JM/MONO(2002)9. Studies conducted in compliance with the above regulations and standards were considered acceptable to US FDA regulatory authorities.

Analysis of Plaque Load in the CNS

The left brain hemispheres of the vehicle treated cynomologus macaque monkeys from the above study were analysed by immunohistochemistry. A coronal section, at the level of the middle temporal sulcus containing portions of the dentate gyrus and hippocampus, was processed into wax as described above. For immunohistochemistry, sections were labelled with a pan-Aβ antibody (1 E8, monoclonal antibody raised to Aβ 13-27), or with the Aβ42 antibody, (20G10, monoclonal antibody recognising Aβ x-42), and labelling was developed as above. A visual count of the number of plaques was taken for each section. Tissue from all five vehicle-treated cynomolgus monkeys showed evidence of parenchymal Aβ plaques. There was also evidence of cerebrovascular labelled Ai and intraneuronal Aβ.

Analysis of Beta Amyloid/Antibody Complexes in Plasma

Biochemical analysis was carried out on plasma samples from two time points (at the end of weeks 4 and 8 after start of dosing) from animals dosed with 50 mg/kg (n=9) or 100 mg/kg (n=10) H2L1, or vehicle dosed controls (n=5). 100 ul duplicate samples were analysed using the commercially available Innogenetics Aβ 1-42 ELISA kit, incubated overnight at 4° C. Control samples were analysed both neat and at 1:10 dilution (using the supplied diluent), while samples from the dosed animals were tested neat and at 1:25. Subsequent absorbance values were analysed, with unknown absorbance values backcalculated to pg/ml values using standard curves, and then corrected for any assay dilution. Total plasma levels of Aβ42 derived from these samples are shown in Table 12 below (figures in pg/ml±SE); all samples from animals treated with H2L1 contained significantly higher levels of Aβ42 (p<0.001 by student t-test) than in control groups.

TABLE 12

|  | Week 4 (pg/ml) | Week 8 (pg/ml) |
| --- | --- | --- |
| Control (1:10) | 104.1 ± 30.4 | 29.8 ± 7.9 |
| 50 mg/kg (1:25) | 830.5 ± 79.1 | 615.8 ± 50.2 |
| 100 mg/kg (1:25) | 1020.5 ± 84.4 | 492.7 ± 46.3 |

Data reported were obtained from diluted samples. Results from the neat samples were not used as many data points were either greater than the top standard, or due to sample volume limitation, only assayed as a single point.

Production Process

Expression vectors encoding H2L1 and operatively linked to amplifiable selection markers such as the DHFR or glutamine synthetase may be used to transfect or transduce appropriate parental CHO cell lines (eg CHODG44 or CHOK 1) to produce engineered cell lines suitable for production of monoclonal antibody at large scale (for review see Bebbington and Hentschel DNA Cloning Volume III; A practical approach (edited by Glover D M) (Oxford IRL press, 1987). In order to increase expression levels the coding sequence maybe codon optimized in order to avoid cis-acting sequence motifs and extreme GC contents (high or low). SEQ. ID Nos:42 and No:43 exemplify such a coding sequence for H2 heavy chain and L1 light chain. Large scale production maybe in stirred tank bioreactors using animal-derived-component-free medium, followed by purification. This may comprise clarification of the harvest, followed by Protein-A affinity chromatography, and further purification using ion (e.g. cation) exchange and mixed mode (e.g. ceramic hydroxyapatite) chromatography unit operations. A virus removal nanofiltration is followed by a final ultrafiltration/diafiltration step that enables formulation suitable for the intended route of administration.

Example of Pharmaceutical Formulation

| Ingredient | Quantity (per mL) |
| --- | --- |
| H2L1 | 50 mg |
| Sodium acetate trihydrate | 6.81 mg |
| Polysorbate 80 | 0.20 mg |
| Arginine base | 10.00 mg |
| Sodium chloride | 3.00 mg |
| Disodium edetate dihydrate | 0.0186 mg |
| Hydrochloric acid | qs to give pH 5.5 |
| Water for Injections | To make 1.0 mL |
| Nitrogen | To fill headspace |

Amino Acid Sequences of V-regions of Acceptor Frameworks and Humanised Variants

M99675 heavy chain acceptor framework V region, amino acid sequence (SEQ ID No: 21)
EVQLVESGGGLVQPGGSLRLSCAASGFTFS<u>SYSMN</u>WVRQAPGKGLEWV
<u>SYISSSSSTIYYADSVKG</u>RFTISRDNAKNSLYLQMNSLRAEDTAVYYC
AR M99675 heavy chain acceptor framework V region DNA (SEQ ID No: 22)
GAGGTGCAGCTGGTGGAGTCTGGGGGAGGCTTGGTACAGCCTGGGGGG
TCCCTGAGACTCTCCTGTGCAGCCTCTGGATTCACCTTCAGTAGCTAT
AGCATGAACTGGGTCCGCCAGGCTCCAGGGAAGGGGCTGGAGTGGGTT
TCATACATTAGTAGTAGTAGTAGTACCATATACTACGCAGACTCTGTG
AAGGGCCGATTCACCATCTCCAGAGACAATGCCAAGAACTCACTGTAT
CTGCAAATGAACAGCCTGAGAGCCGAGGACACGGCTGTGTATTACTGT
GCGAGAGA CAA51135 light chain acceptor framework V region amino acid sequence (SEQ ID No: 24)
DIVMTQSPLSLPVTPGEPASISC<u>RSSQSLLHSNGYNYLD</u>WYLQKPGQS
PQLLIY<u>LGSNRAS</u>GVPDRFSGSGSGTDFTLKISRVEAEDVGVYYC<u>MQ
ALQTPWT</u>FGQGTKVEIK CAA51135 light chain acceptor framework V region DNA (SEQ ID No: 25)
GATATTGTGATGACTCAGTCTCCACTCTCCCTGCCCGTCACCCCTGGA
GAGCCGGCCTCCATCTCCTGCAGGTCTAGTCAGAGCCTCCTGCATAGT
AATGGATACAACTATTTGGATTGGTACCTGCAGAAGCCAGGGCAGTCT

Amino Acid Sequences of V-regions of Acceptor Frameworks and Humanised Variants CCACAGCTCCTGATCTATTTGGGTTCTAATCGGGCCTCCGGGGTCCCT
GACAGGTTCAGTGGCAGTGGATCAGGCACAGATTTTACACTGAAAATC
AGCAGAGTGGAGGCTGAGGATGTTGGGGTTTATTACTGCATGCAAGCT
CTACAAACTCCGTGGACGTTCGGCCAAGGGACCAAGGTGGAAATCAAA Humanised heavy chain V region variant H1, amino acid sequence
(SEQ ID No: 26)
EVQLVESGGGLVQPGGSLRLSCAASGFTFS<u>DNGMA</u>WVRQAPGKGLEWV
<u>SFISNLAYSIDYADTVTGR</u>FTISRDNAKNSLYLQMNSLRAEDTAVYYC
VS<u>GTWFAY</u>WGQGTLVTVSS Humanised heavy chain V region variant H1 DNA coding sequence
(SEQ ID No: 27)
GAGGTGCAGCTGGTGGAGTCTGGGGGAGGCTTGGTACAGCCTGGGGGG
TCCCTGAGACTCTCCTGTGCAGCCTCTGGATTCACCTTCAGTGACAAC
GGAATGGCGTGGGTCCGCCAGGCTCCAGGGAAGGGGCTGGAGTGGGTT
TCATTCATTAGTAATTTGGCATATAGTATCGACTACGCAGACACTGTG
ACGGGCCGATTCACCATCTCCAGAGACAATGCCAAGAACTCACTGTAT
CTGCAAATGAACAGCCTGAGAGCCGAGGACACGGCTGTGTATTACTGT
GTCAGCGGGACCTGGTTTGCTTACTGGGGCCAGGGCACACTAGTCACA
GTCTCCTCA Humanised heavy chain V region variant H2, amino acid sequence
(SEQ ID No: 28)
EVQLVESGGGLVQPGGSLRLSCAVSGFTFS<u>DNGMA</u>WVRQAPGKGLEWV
<u>SFISNLAYSIDYADTVTGR</u>FTISRDNAKNSLYLQMNSLRAEDTAVYYC
VS<u>GTWFAY</u>WGQGTLVTVSS Humanised heavy chain V region variant H2 DNA
(SEQ ID No: 29)
GAGGTGCAGCTGGTGGAGTCTGGGGGAGGCTTGGTACAGCCTGGGGGG
TCCCTGAGACTCTCCTGTGCAGTCTCTGGATTCACCTTCAGTGACAAC
GGAATGGCGTGGGTCCGCCAGGCTCCAGGGAAGGGGCTGGAGTGGGTT
TCATTCATTAGTAATTTGGCATATAGTATCGACTACGCAGACACTGTG
ACGGGCCGATTCACCATCTCCAGAGACAATGCCAAGAACTCACTGTAT
CTGCAAATGAACAGCCTGAGAGCCGAGGACACGGCTGTGTATTACTGT
GTCAGCGGGACCTGGTTTGCTTACTGGGGCCAGGGCACACTAGTCACA
GTCTCCTCA Humanised heavy chain V region variant H3, amino acid sequence
(SEQ ID No: 30)
EVQLVESGGGLVQPGGSLRLSCAASGFTFS<u>DNGMA</u>WVRQAPGKGLEWI
<u>SFISNLAYSIDYADTVTGR</u>FTISRDNAKNSLYLQMNSLRAEDTAVYYC
VS<u>GTWFAY</u>WGQGTLVTVSS Humanised heavy chain V region variant H3 DNA
(SEQ ID No: 31)
GAGGTGCAGCTGGTGGAGTCTGGGGGAGGCTTGGTACAGCCTGGGGGG
TCCCTGAGACTCTCCTGTGCAGCCTCTGGATTCACCTTCAGTGACAAC
GGAATGGCGTGGGTCCGCCAGGCTCCAGGGAAGGGGCTGGAGTGGATC
TCATTCATTAGTAATTTGGCATATAGTATCGACTACGCAGACACTGTG
ACGGGCCGATTCACCATCTCCAGAGACAATGCCAAGAACTCACTGTAT
CTGCAAATGAACAGCCTGAGAGCCGAGGACACGGCTGTGTATTACTGT
GTCAGCGGGACCTGGTTTGCTTACTGGGGCCAGGGCACACTAGTCACA
GTCTCCTCA Humanised light chain V region variant L1 amino acid sequence
(SEQ ID No: 32)
DIVMTQSPLSLPVTPGEPASISC<u>RVSQSLLHSNGYTYLH</u>WYLQKPGQS
PQLLIY<u>KVSNRFS</u>GVPDRFSGSGSGTDFTLKISRVEAEDVGVYYC<u>SQT
RHVPYT</u>FGGGTKVEIK Humanised light chain V region variant L1 DNA
(SEQ ID No: 33)
GATATTGTGATGACTCAGTCTCCACTCTCCCTGCCCGTCACCCCTGGA
GAGCCGGCCTCCATCTCCTGCAGAGTTAGTCAGAGCCTTTTACACAGT
AATGGATACACCTATTTACATTGGTACCTGCAGAAGCCAGGGCAGTCT
CCACAGCTCCTGATCTATAAAGTTTCCAACCGATTTTCTGGGGTCCCT
GACAGGTTCAGTGGCAGTGGATCAGGCACAGATTTTACACTGAAAATC
AGCAGAGTGGAGGCTGAGGATGTTGGGGTTTATTACTGCTCTCAAACT
AGACATGTTCCGTACACGTTCGGCGGAGGGACCAAGGTGGAAATCAAA Mature H1 heavy chain amino acid sequence (Fc mutated double mutation bold)
(SEQ ID No: 34)
EVQLVESGGGLVQPGGSLRLSCAASGFTFS<u>DNGMA</u>WVRQAPGKGLEWV
<u>SFISNLAYSIDYADTVTGR</u>FTISRDNAKNSLYLQMNSLRAEDTAVYYC
VS<u>GTWFAY</u>WGQGTLVTVSSASTKGPSVFPLAPSSKSTSGGTAALGCLV
KDYFPEPVTVSWNSGALTSGVHTFPAVLQSSGLYSLSSVVTVPSSSLG
TQTYICNVNHKPSNTKVDKKVEPKSCDKTHTCPPCPAPELAGAPSVFL
FPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHN
HYTQKSLSLSPGK H1 Full length DNA
(SEQ ID No: 35)
GAGGTGCAGCTGGTGGAGTCTGG
GGGAGGCTTGGTACAGCCTGGGGGGTCCCTGAGACTCTCCTGTGCAGC
CTCTGGATTCACCTTCAGTGACAACGGAATGG
CGTGGGTCCGCCAGGCTCCAGGGAAGGGGCTGGAGTGGGTTTCATTCA
TTAGTAATTTGGCATATAGTATCGACTACGCA
GACACTGTGACGGGCCGATTCACCATCTCCAGAGACAATGCCAAGAAC
TCACTGTATCTGCAAATGAACAGCCTGAGAGC
CGAGGACACGGCTGTGTATTACTGTGTCAGCGGGACCTGGTTTGCTTA
CTGGGGCCAGGGCACACTAGTCACAGTCTCCT
CAGCCTCCACCAAGGGCCCATCGGTCTTCCCCCTGGCACCCTCCTCCA
AGAGCACCTCTGGGGGCACAGCGGCCCTGGGC
TGCCTGGTCAAGGACTACTTCCCCGAACCGGTGACGGTGTCGTGGAAC
TCAGGCGCCCTGACCAGCGGCGTGCACACCTT
CCCGGCTGTCCTACAGTCCTCAGGACTCTACTCCCTCAGCAGCGTGGT
GACCGTGCCCTCCAGCAGCTTGGGCACCCAGA
CCTACATCTGCAACGTGAATCACAAGCCCAGCAACACCAAGGTGGACA
AGAAAGTTGAGCCCAAATCTTGTGACAAAACT
CACACATGCCCACCGTGCCCAGCACCTGAACTCGCGGGGGCACCGTCA
GTCTTCCTCTTCCCCCCAAAACCCAAGGACAC
CCTCATGATCTCCCGGACCCCTGAGGTCACATGCGTGGTGGTGGACGT
GAGCCACGAAGACCCTGAGGTCAAGTTCAACT
GGTACGTGGACGGCGTGGAGGTGCATAATGCCAAGACAAAGCCGCGGG
AGGAGCAGTACAACAGCACGTACCGTGTGGTC
AGCGTCCTCACCGTCCTGCACCAGGACTGGCTGAATGGCAAGGAGTAC
AAGTGCAAGGTCTCCAACAAAGCCCTCCCAGC
CCCCATCGAGAAAACCATCTCCAAAGCCAAAGGGCAGCCCCGAGAACC
ACAGGTGTACACCCTGCCCCCATCCCGGGATG
AGCTGACCAAGAACCAGGTCAGCCTGACCTGCCTGGTCAAAGGCTTCT
ATCCCAGCGACATCGCCGTGGAGTGGGAGAGC
AATGGGCAGCCGGAGAACAACTACAAGACCACGCCTCCCGTGCTGGAC
TCCGACGGCTCCTTCTTCCTCTACAGCAAGCT
CACCGTGGACAAGAGCAGGTGGCAGCAGGGGAACGTCTTCTCATGCTC
CGTGATGCATGAGGCTCTGCACAACCACTACA
CGCAGAAGAGCCTCTCCCTGTCTCCGGGTAAA Mature H2 heavy chain amino acid sequence, (Fc mutated double mutation bold)
(SEQ ID No: 36)
EVQLVESGGGLVQPGGSLRLSCAVSGFTFS<u>DNGMA</u>WVRQAPGKGLEWV
<u>SFISNLAYSIDYADTVTGR</u>FTISRDNAKNSLYLQMNSLRAEDTAVYYC
VS<u>GTWFAY</u>WGQGTLVTVSSASTKGPSVFPLAPSSKSTSGGTAALGCLV
KDYFPEPVTVSWNSGALTSGVHTFPAVLQSSGLYSLSSVVTVPSSSLG
TQTYICNVNHKPSNTKVDKKVEPKSCDKTHTCPPCPAPELAGAPSVFL
FPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHN
HYTQKSLSLSPGK H2 Full length DNA
(SEQ ID No: 37)
GAGGTGCAGCTGGTGGAGTCTGGGGGAGGCTTGGTACAGCCTGGGGGG
TCCCTGAGACTCTCCTGTGCAGTCTCTGGATT
CACCTTCAGTGACAACGGAATGGCGTGGGTCCGCCAGGCTCCAGGGAA
GGGGCTGGAGTGGGTTTCATTCATTAGTAATT
TGGCATATAGTATCGACTACGCAGACACTGTGACGGGCCGATTCACCA
TCTCCAGAGACAATGCCAAGAACTCACTGTAT
CTGCAAATGAACAGCCTGAGAGCCGAGGACACGGCTGTGTATTACTGT
GTCAGCGGGACCTGGTTTGCTTACTGGGGCCA

Amino Acid Sequences of V-regions of Acceptor Frameworks and Humanised Variants GGGCACACTAGTCACAGTCTCCTCAGCCTCCACCAAGGGCCCATCGGT
CTTCCCCCTGGCACCCTCCTCCAAGAGCACCT
CTGGGGGCACAGCGGCCTCGGGCTGCCTGGTCAAGGACTACTTCCCCG
AACCGGTGACGGTGTCGTGGAACTCAGGCGCC
CTGACCAGCGGCGTGCACACCTTCCCGGCTGTCCTACAGTCCTCAGGA
CTCTACTCCCTCAGCAGCGTGGTGACCGTGCC
CTCCAGCAGCTTGGGCACCCAGACCTACATCTGCAACGTGAATCACAA
GCCCAGCAACACCAAGGTGGACAAGAAAGTTG
AGCCCAAATCTTGTGACAAAACTCACACATGCCCACCGTGCCCAGCAC
CTGAACTCGCGGGGGCACCGTCAGTCTTCCTC
TTCCCCCCAAAACCCAAGGACACCCTCATGATCTCCCGGACCCCTGAG
GTCACATGCGTGGTGGTGGACGTGAGCCACGA
AGACCCTGAGGTCAAGTTCAACTGGTACGTGGACGGCGTGGAGGTGCA
TAATGCCAAGACAAAGCCGCGGGAGGAGCAGT
ACAACAGCACGTACCGTGTGGTCAGCGTCCTCACCGTCCTGCACCAGG
ACTGGCTGAATGGCAAGGAGTACAAGTGCAAG
GTCTCCAACAAAGCCCTCCCAGCCCCCATCGAGAAAACCATCTCCAAA
GCCAAAGGGCAGCCCCGAGAACCACAGGTGTA
CACCCTGCCCCCATCCCGGGATGAGCTGACCAAGAACCAGGTCAGCCT
GACCTGCCTGGTCAAAGGCTTCTATCCCAGCG
ACATCGCCGTGGAGTGGGAGAGCAATGGGCAGCCGGAGAACAACTACA
AGACCACGCCTCCCGTGCTGGACTCCGACGGC
TCCTTCTTCCTCTACAGCAAGCTCACCGTGGACAAGAGCAGGTGGCAG
CAGGGGAACGTCTTCTCATGCTCCGTGATGCA
TGAGGCTCTGCACAACCACTACACGCAGAAGAGCCTCTCCCTGTCTCC
GGGTAAA Mature H3 heavy chain amino acid sequence
(Fc mutated double mutation bold)
(SEQ ID No: 38)
EVQLVESGGGLVQPGGSLRLSCAASGFTFS<u>DNGMA</u>WVRQAPGKGLEWI
S<u>FISNLAYSIDYADTVT</u>GRFTISRDNAKNSLYLQMNSLRAEDTAVYYC
VS<u>GTWFAY</u>WGQGTLVTVSSASTKGPSVFPLAPSSKSTSGGTAALGCLV
KDYFPEPVTVSWNSGALTSGVHTFPAVLQSSGLYSLSSVVTVPSSSLG
TQTYICNVNHKPSNTKVDKKVEPKSCDKTHTCPPCPAPELAGAPSVFL
FPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHN
HYTQKSLSLSPGK H3 full length DNA
(SEQ ID No: 39)
GAGGTGCAGCTGGTGGAGTCTGGGGGAGGCTTGGTACAGCCTGGGGGG
TCCCTGAGACTCTCCTGTGCAGCCTCTGGATTCACCTTCAGTGACAAC
GGAATGGCGTGGGTCCGCCAGGCTCCAGGGAAGGGGCTGGAGTGGATC
TCATTCATTAGTAATTTGGCATATAGTATCGACTACGCAGACACTGTG
ACGGGCCGATTCACCATCTCCAGAGACAATGCCAAGAACTCACTGTAT
CTGCAAATGAACAGCCTGAGAGCCGAGGACACGGCTGTGTATTACTGT
GTCAGCGGGACCTGGTTTGCTTACTGGGGCCAGGGCACACTAGTCACA
GTCTCCTCAGCCTCCACCAAGGGCCCATCGGTCTTCCCCCTGGCACCC
TCCTCCAAGAGCACCTCTGGGGGCACAGCGGCCCTGGGCTGCCTGGTC
AAGGACTACTTCCCCGAACCGGTGACGGTGTCGTGGAACTCAGGCGCC
CTGACCAGCGGCGTGCACACCTTCCCGGCTGTCCTACAGTCCTCAGGA
CTCTACTCCCTCAGCAGCGTGGTGACCGTGCCCTCCAGCAGCTTGGGC
ACCCAGACCTACATCTGCAACGTGAATCACAAGCCCAGCAACACCAAG
GTGGACAAGAAAGTTGAGCCCAAATCTTGTGACAAAACTCACACATGC
CCACCGTGCCCAGCACCTGAACTCGCGGGGGCACCGTCAGTCTTCCTC
TTCCCCCCAAAACCCAAGGACACCCTCATGATCTCCCGGACCCCTGAG
GTCACATGCGTGGTGGTGGACGTGAGCCACGAAGACCCTGAGGTCAAG
TTCAACTGGTACGTGGACGGCGTGGAGGTGCATAATGCCAAGACAAAG
CCGCGGGAGGAGCAGTACAACAGCACGTACCGTGTGGTCAGCGTCCTC
ACCGTCCTGCACCAGGACTGGCTGAATGGCAAGGAGTACAAGTGCAAG
GTCTCCAACAAAGCCCTCCCAGCCCCCATCGAGAAAACCATCTCCAAA
GCCAAAGGGCAGCCCCGAGAACCACAGGTGTACACCCTGCCCCCATCC
CGGGATGAGCTGACCAAGAACCAGGTCAGCCTGACCTGCCTGGTCAAA
GGCTTCTATCCCAGCGACATCGCCGTGGAGTGGGAGAGCAATGGGCAG
CCGGAGAACAACTACAAGACCACGCCTCCCGTGCTGGACTCCGACGGC
TCCTTCTTCCTCTACAGCAAGCTCACCGTGGACAAGAGCAGGTGGCAG
CAGGGGAACGTCTTCTCATGCTCCGTGATGCATGAGGCTCTGCACAAC
CACTACACGCAGAAGAGCCTCTCCCTGTCTCCGGGTAAA Mature Light chain amino acid sequence
(SEQ ID No: 40)
DIVMTQSPLSLPVTPGEPASISC<u>RVSQSLLHSNGYTYLH</u>WYLQKPGQS
PQLLIY<u>KVSNRFS</u>GVPDRFSGSGSGTDFTLKISRVEAEDVGVYYC<u>SQT
RHVPYT</u>FGGGTKVEIKRTVAAPSVFIFPPSDEQLKSGTASVVCLLNNF
YPREAKVQWKVDNALQSGNSQESVTEQDSKDSTYSLSSTLTLSKADYE
KHKVYACEVTHQGLSSPVTKSFNRGEC L1 Full length DNA
(SEQ ID No: 41)
GATATTGTGATGACTCAGTCTCCACTCTCCCTGCCCGTCACCCCTGGA
GAGCCGGCCTCCATCTCCTGCAGAGTTAGTCAGAGCCTTTTACACAGT
AATGGATACACCTATTTACATTGGTACCTGCAGAAGCCAGGGCAGTCT
CCACAGCTCCTGATCTATAAAGTTTCCAACCGATTTTCTGGGGTCCCT
GACAGGTTCAGTGGCAGTGGATCAGGCACAGATTTTACACTGAAAATC
AGCAGAGTGGAGGCTGAGGATGTTGGGGTTTATTACTGCTCTCAAACT
AGACATGTTCCGTACACGTTCGGCGGAGGGACCAAGGTGGAAATCAAA
CGTACGGTGGCTGCACCATCTGTCTTCATCTTCCCGCCATCTGATGAG
CAGTTGAAATCTGGAACTGCCTCTGTTGTGTGCCTGCTGAATAACTTC
TATCCCAGAGAGGCCAAAGTACAGTGGAAGGTGGACAACGCCCTCCAA
TCGGGTAACTCCCAGGAGAGTGTCACAGAGCAGGACAGCAAGGACAGC
ACCTACAGCCTCAGCAGCACCCTGACGCTGAGCAAAGCAGACTACGAG
AAACACAAAGTCTACGCCTGCGAAGTCACCCATCAGGGCCTGAGCTCG
CCCGTCACAAAGAGCTTCAACAGGGGAGAGTGT Optimised H2 heavy chain DNA
(SEQ ID No: 42)
GAGGTGCAGCTGGTGGAGTCTGGCGGCGGACTGGTGCAGCCTGGCGGC
AGCCTGAGACTGAGCTGTGCCGTGTCCGGCTTCACCTTCAGCGACAAC
GGCATGGCCTGGGTGAGGCAGGCCCCTGGCAAGGGCCTGGAGTGGGTG
TCCTTCATCAGCAACCTGGCCTACAGCATCGACTACGCCGACACCGTG
ACCGGCAGATTCACCATCAGCCGGGACAACGCCAAGAACAGCCTGTAC
CTGCAGATGAACAGCCTGAGAGCCGAGGACACCGCCGTGTACTACTGT
GTGAGCGGCACCTGGTTCGCCTACTGGGGCCAGGGCACCCTGGTGACC
GTGTCCAGCGCCAGCACCAAGGGCCCCAGCGTGTTCCCCCTGGCCCCC
AGCAGCAAGAGCACCAGCGGCGGCACAGCCGCCCTGGGCTGCCTGGTG
AAGGACTACTTCCCCGAACCGGTGACCGTGTCCTGGAACAGCGGAGCC
CTGACCAGCGGCGTGCACACCTTCCCCGCCGTGCTGCAGAGCAGCGGC
CTGTACAGCCTGAGCAGCGTGGTGACCGTGCCCAGCAGCAGCCTGGGC
ACCCAGACCTACATCTGTAACGTGAACCACAAGCCCAGCAACACCAAG
GTGGACAAGAAGGTGGAGCCCAAGAGCTGTGACAAGACCCACACCTGC
CCCCCCTGCCCTGCCCCCGAGCTGGCCGGAGCCCCCAGCGTGTTCCTG
TTCCCCCCCAAGCCTAAGGACACCCTGATGATCAGCAGAACCCCCGAG
GTGACCTGTGTGGTGGTGGATGTGAGCCACGAGGACCCTGAGGTGAAG
TTCAACTGGTACGTGGACGGCGTGGAGGTGCACAATGCCAAGACCAAG
CCCAGGGAGGAGCAGTACAACAGCACCTACCGGGTGGTGTCCGTGCTG
ACCGTGCTGCACCAGGATTGGCTGAACGGCAAGGAGTACAAGTGTAAG
GTGTCCAACAAGGCCCTGCCTGCCCCTATCGAGAAAACCATCAGCAAG
GCCAAGGGCCAGCCCAGAGAGCCCCAGGTGTACACCCTGCCCCCTAGC
AGAGATGAGCTGACCAAGAACCAGGTGTCCCTGACCTGCCTGGTGAAG
GGCTTCTACCCCAGCGACATCGCCGTGGAGTGGGAGAGCAACGGCCAG
CCCGAGAACAACTACAAGACCACCCCCCCTGTGCTGGACAGCGATGGC
AGCTTCTTCCTGTACAGCAAGCTGACCGTGGACAAGAGCAGATGGCAG
CAGGGCAACGTGTTCAGCTGCTCCGTGATGCACGAGGCCCTGCACAAT
CACTACACCCAGAAGAGCCTGAGCCTGTCCCCTGGCAAG Optimised L1 light chain DNA
(SEQ ID No: 43)
GACATCGTGATGACCCAGAGCCCCCTGAGCCTGCCCGTGACCCCTGGC
GAGCCCGCCAGCATCAGCTGTAGAGTGAGCCAGAGCCTGCTGCACAGC
AACGGCTACACCTACCTGCACTGGTATCTGCAGAAGCCTGGCCAGAGC
CCTCAGCTGCTGATCTACAAAGTGTCCAACCGGTTCAGCGGCGTGCCT
GATAGATTCAGCGGCAGCGGCTCCGGCACCGACTTCACCCTGAAGATC
AGCAGAGTGGAGGCCGAGGATGTGGGCGTGTACTACTGCTCCCAGACC
AGACACGTGCCTTACACCTTTGGCGGCGGAACAAAGGTGGAGATCAAG
CGTACGGTGGCCGCCCCCAGCGTGTTCATCTTCCCCCCCAGCGATGAG
CAGCTGAAGAGCGGCACCGCCAGCGTGGTGTGTCTGCTGAACAACTTC
TACCCCCGGGAGGCCAAGGTGCAGTGGAAGGTGGACAATGCCCTGCAG
AGCGGCAACAGCCAGGAGAGCGTGACCGAGCAGGACAGCAAGGACTCC
ACCTACAGCCTGAGCAGCACCCTGACCCTGAGCAAGGCCGACTACGAG
AAGCACAAGGTGTACGCCTGTGAGGTGACCCACCAGGGCCTGTCCAGC
CCCGTGACCAAGAGCTTCAACCGGGGCGAGTGC

The invention claimed is:

1. An isolated therapeutic antibody which is an antibody or antigen binding fragment which binds β-amyloid peptide and which comprises the following CDRs:
CDRH1: DNGMA (SEQ ID No:1)
CDRH2: FISNLAYSIDYADTVTG (SEQ ID No:2)
CDRH3: GTWFAY (SEQ ID No:3)
within a human heavy chain variable region originating from the VH3 gene family and:
CDRL1: RVSQSLLHSNGYTYLH (SEQ ID No:4)
CDRL2: KVSNRFS (SEQ ID No:5)
CDRL3: SQTRHVPYT (SEQ ID No:6)
within a human light chain variable region originating from the amino acid sequence disclosed in GenPept entry CAA51135 (SEQ ID No:24).

2. An isolated therapeutic antibody according to claim 1, in which the human heavy chain variable region originates from a V gene selected from the group consisting of: VH3-48, VH3-21, VH3-11, VH3-7, VH3-13, VH3-74, VH3-64, VH3-23, VH3-38, VH3-53, VH3-66, VH3-20, VH3-9 and VH3-43.

3. An isolated therapeutic antibody according to claim 2 having a human acceptor heavy chain framework of M99675 (SEQ ID No:21) together with a framework 4.

4. An isolated therapeutic antibody according to claim 3, in which the framework 4 sequence is that encoded by the human JH4 minigene (Kabat):
YFDYWGQGTLVTVSS (SEQ ID No:23)
of which the initial four residues fall within the CDR3 region is replaced by the incoming CDR from a donor antibody.

5. An isolated therapeutic antibody according to claim 1 which contains one or more substitutions of amino acid residues based on the corresponding residues found in a donor $V_H$ domain having the sequence: SEQ ID No:17 and $V_L$ domain having the sequence: SEQ ID No: 19 that maintain all or substantially all of the binding affinity of the donor antibody for β-amyloid peptide.

6. An isolated therapeutic antibody according to claim 5 having a human acceptor heavy chain framework of M99675 together with JH4 containing one to four amino acid residue substitutions selected from positions 24, 48, 93 and/or 94 (Kabat numbering).

7. An isolated therapeutic antibody according to claim 6 having a human acceptor heavy chain framework which comprises the following residues:

| Position | Residue |
|---|---|
| (i) | |
| 93 | V |
| 94 | S |
| or (ii) | |
| 24 | V |
| 93 | V |
| 94 | S |
| or (iii) | |
| 48 | I |
| 93 | V |
| 94 | S. |

8. An isolated therapeutic antibody which binds β-amyloid peptide comprising a $V_H$ chain having the sequence set forth in SEQ ID No:26 and a $V_L$ domain having the sequence set forth in SEQ ID No:32.

9. An isolated therapeutic antibody which binds β-amyloid peptide comprising a $V_H$ chain having the sequence set forth in SEQ ID No: 28 and a $V_L$ domain having the sequence set forth in SEQ ID No:32.

10. An isolated therapeutic antibody which binds β-amyloid peptide comprising a $V_H$ chain having the sequence set forth in SEQ ID No:30 and a $V_L$ domain having the sequence set forth in SEQ ID No:32.

11. An isolated therapeutic antibody which is an antibody or antigen binding fragment which binds β-amyloid peptide 1-12 (SEQ ID No:15) with equilibrium constant KD less than 100 pM and has an equilibrium constant KD for binding to β-amyloid peptide 2-13 (SEQ ID No:44) which is 1000-fold greater than that for peptide 1-12 (SEQ ID No:15), both determinations being made in a surface plasmon resonance assay utilising peptide captured on streptavidin chip.

12. An isolated therapeutic antibody which is an antibody or antigen binding fragment which binds β-amyloid peptide 1-40 with equilibrium constant KD less than 10 nM and has an equilibrium constant KD for binding to β-amyloid peptide 2-13 (SEQ ID No:44) which is 1000-fold greater than that for peptide 1-12 (SEQ ID No:15), both determinations being made in the surface plasmon resonance assay described in Method B of the Examples.

13. An isolated therapeutic antibody according claim 1 which is of IgG1 isotype.

14. An isolated therapeutic antibody according to claim 1 which essentially lacks the functions of a) activation of complement by the classical pathway; and b) mediating antibody-dependent cellular cytotoxicity.

15. An isolated therapeutic antibody according to claim 13 in which residues 235 and 237 have been mutated to alanine.

16. An isolated therapeutic antibody according to claim 1, which antibody comprises a heavy chain having the sequence set forth in SEQ ID No:34, 36 or 38 and a light chain having the sequence set forth in SEQ ID No:40.

17. A pharmaceutical composition comprising an isolated therapeutic antibody according to claim 1.

18. An isolated antibody or a fragment thereof which binds β-amyloid peptide comprising a $V_H$ domain having the sequence: SEQ ID No:17 and a $V_L$ domain having the sequence: SEQ ID No: 19.

* * * * *